US008222397B2

(12) United States Patent
Bitner

(10) Patent No.: US 8,222,397 B2
(45) Date of Patent: Jul. 17, 2012

(54) METHODS OF OPTIMAL PURIFICATION OF NUCLEIC ACIDS AND KIT FOR USE IN PERFORMING SUCH METHODS

(75) Inventor: Rex M. Bitner, Cedarburg, WI (US)

(73) Assignee: Promega Corporation, Madison, WI (US)

(*) Notice: Subject to any disclaimer, the term of this patent is extended or adjusted under 35 U.S.C. 154(b) by 256 days.

(21) Appl. No.: 12/549,685

(22) Filed: Aug. 28, 2009

(65) Prior Publication Data
US 2011/0054157 A1   Mar. 3, 2011

(51) Int. Cl.
C07H 21/04 (2006.01)
(52) U.S. Cl. .................. 536/25.41; 536/25.42
(58) Field of Classification Search .............. 536/25.41, 536/25.42
See application file for complete search history.

(56) References Cited

U.S. PATENT DOCUMENTS

| | | |
|---|---|---|
| 3,389,133 A | 6/1968 | Gutcho |
| 3,652,761 A | 3/1972 | Weetall |
| 3,897,309 A | 7/1975 | Grabner |
| 4,059,512 A | 11/1977 | Harris |
| 4,224,413 A | 9/1980 | Burbidge |
| 4,233,169 A | 11/1980 | Beall et al. |
| 4,297,337 A | 10/1981 | Mansfield et al. |
| 4,298,500 A | 11/1981 | Abbott |
| 4,395,271 A | 7/1983 | Beall et al. |
| 4,491,660 A | 1/1985 | Gendrich et al. |
| 4,523,996 A | 6/1985 | Charles et al. |
| 4,554,088 A | 11/1985 | Whitehead et al. |
| 4,659,678 A | 4/1987 | Forrest et al. |
| 4,661,260 A | 4/1987 | Kodama et al. |
| 4,661,407 A | 4/1987 | Henderson |
| 4,672,040 A | 6/1987 | Josephson |
| 4,683,202 A | 7/1987 | Mullis |
| 4,695,393 A | 9/1987 | Whitehead et al. |
| 4,699,717 A | 10/1987 | Riesner et al. |
| 4,743,545 A | 5/1988 | Torobin |
| 4,767,670 A | 8/1988 | Cox et al. |
| 4,780,423 A | 10/1988 | Bluestein et al. |
| 4,808,314 A | 2/1989 | Karplus et al. |
| 4,861,705 A | 8/1989 | Margel |
| 4,866,034 A | 9/1989 | Ribi |
| 4,885,168 A | 12/1989 | Hashimoto et al. |
| 4,921,805 A | 5/1990 | Gebeyehu et al. |
| 4,925,818 A | 5/1990 | Schneider et al. |
| 4,927,749 A | 5/1990 | Dorn |
| 4,927,750 A | 5/1990 | Dorn |
| 4,935,342 A | 6/1990 | Seligson et al. |
| 4,966,613 A | 10/1990 | Beaver |
| 5,039,559 A | 8/1991 | Sang et al. |
| 5,057,426 A | 10/1991 | Henco et al. |
| 5,059,527 A | 10/1991 | White et al. |
| 5,075,430 A | 12/1991 | Little |
| 5,076,950 A | 12/1991 | Ullman et al. |
| 5,126,239 A | 6/1992 | Livak et al. |
| 5,155,018 A | 10/1992 | Gillespie et al. |
| 5,169,535 A | 12/1992 | Adachi et al. |
| 5,234,809 A | 8/1993 | Boom et al. |
| 5,316,680 A | 5/1994 | Frechet et al. |
| 5,346,994 A | 9/1994 | Chomczynski |
| 5,389,449 A | 2/1995 | Afeyan et al. |
| 5,395,498 A | 3/1995 | Gombinsky et al. |
| 5,401,415 A | 3/1995 | Rauh et al. |
| 5,403,917 A | 4/1995 | Boos et al. |
| 5,437,983 A | 8/1995 | Watts et al. |
| 5,482,834 A | 1/1996 | Gillespie |
| 5,491,083 A | 2/1996 | Arentzen et al. |
| 5,512,439 A | 4/1996 | Hornes et al. |
| 5,523,231 A | 6/1996 | Reeve |
| 5,561,064 A | 10/1996 | Marquet et al. |
| 5,563,068 A | 10/1996 | Zhang et al. |
| 5,564,104 A | 10/1996 | Pourfarzaneh |
| 5,576,185 A | 11/1996 | Coulter et al. |
| 5,582,988 A | 12/1996 | Backus et al. |
| 5,585,236 A | 12/1996 | Bonn et al. |
| 5,589,459 A | 12/1996 | Porro |
| 5,591,628 A | 1/1997 | Baek et al. |
| 5,610,274 A | 3/1997 | Wong et al. |
| 5,639,599 A | 6/1997 | Ryder et al. |

(Continued)

FOREIGN PATENT DOCUMENTS
AU        707115       1/1997
(Continued)

OTHER PUBLICATIONS

Abbaszadagan et al., "Detection of enteroviruses in groundwater with the [CT," Appl. Environ. Microbiol. (1993) 59(5):1318-1324.

Advertisement, Promega Corporation Nucleic Acid purification products, "Having trouble seeing how to optimize your nucleic acid purification process?" Nature Biotechnology, vol. 19, No. 5, May 2001 (9228-AD-HT).

Advertisement, Wizard® Nucleic Acid Purification Systems, Science, vol. 282, Dec. 4, 1998. (Wizard® PureFection Plasmid DNA Purification System and PolyATtract® mRNA Isolation Systems) 2 pages.

Advertisement, Wizard® PureFection Plasmid DNA Purification System, Science, vol. 282, Oct. 30, 1998.

Ahn, S.C. et al., "Rapid mini-scale plasmid isolation for DNA sequencing and restriction mapping," BioTechniques (2000) 29:466-468.

(Continued)

Primary Examiner — Kenneth R. Horlick
(74) Attorney, Agent, or Firm — Michael Best & Friedrich LLP

(57) ABSTRACT

A method and kit which allow the use of a discrete amount of a binding matrix to first purify nucleic acids from a medium under a first set of binding conditions wherein the amount of nucleic acid bound to the binding matrix is essentially independent of the amount of surface area of the definable amount of the binding matrix, followed by a second purification step wherein the nucleic acids are bound to a discrete amount of binding matrix under a second set of binding conditions wherein the amount of nucleic acid bound to the binding matrix is essentially dependent on the amount of surface area of the definable amount of the binding matrix, thus providing a discrete quantity of nucleic acid.

8 Claims, 9 Drawing Sheets

U.S. PATENT DOCUMENTS

| | | | | |
|---|---|---|---|---|
| 5,652,348 | A | 7/1997 | Burton et al. | |
| 5,654,141 | A | 8/1997 | Mariani et al. | |
| 5,658,548 | A | 8/1997 | Padhye et al. | |
| 5,660,984 | A | 8/1997 | Davis et al. | |
| 5,674,997 | A | 10/1997 | Woodard et al. | |
| 5,681,946 | A | 10/1997 | Reeve | |
| 5,683,875 | A | 11/1997 | Lichtenwalter et al. | |
| 5,693,785 | A | 12/1997 | Woodard et al. | |
| 5,705,628 | A | 1/1998 | Hawkins | 536/25.4 |
| 5,728,822 | A | 3/1998 | Macfarlane | |
| 5,734,020 | A | 3/1998 | Wong et al. | |
| 5,746,978 | A | 5/1998 | Bienhaus et al. | |
| 5,747,663 | A | 5/1998 | Colpan et al. | |
| 5,783,686 | A | 7/1998 | Gonzalez | |
| 5,789,148 | A | 8/1998 | Van Vlasselaer et al. | |
| 5,790,964 | A | 8/1998 | Pourfarzaneh | |
| 5,792,651 | A | 8/1998 | Colpan et al. | |
| 5,804,684 | A | 9/1998 | Su | |
| 5,808,041 | A | 9/1998 | Padhye et al. | |
| 5,861,315 | A | 1/1999 | Nakahata | |
| 5,898,071 | A | 4/1999 | Hawkins | 536/25.4 |
| 5,904,848 | A | 5/1999 | Wong et al. | |
| 5,945,525 | A | 8/1999 | Uematsu et al. | |
| 5,973,138 | A | 10/1999 | Collis et al. | |
| 5,981,235 | A | 11/1999 | Shultz et al. | |
| 5,990,301 | A | 11/1999 | Colpan et al. | |
| 6,027,945 | A | 2/2000 | Smith et al. | 436/526 |
| 6,045,697 | A | 4/2000 | Girot et al. | |
| 6,048,695 | A | 4/2000 | Bradley et al. | |
| 6,051,380 | A | 4/2000 | Sosnowski et al. | |
| 6,084,091 | A | 7/2000 | Muller et al. | |
| 6,103,127 | A | 8/2000 | Pourfarzaneh | |
| 6,117,398 | A | 9/2000 | Bienhaus et al. | |
| 6,156,504 | A | 12/2000 | Gocke et al. | |
| 6,180,778 | B1 | 1/2001 | Bastian et al. | |
| 6,194,562 | B1 | 2/2001 | Smith et al. | |
| 6,218,531 | B1 | 4/2001 | Ekenberg | |
| 6,255,477 | B1 | 7/2001 | Kleiber et al. | |
| 6,270,970 | B1 | 8/2001 | Smith et al. | |
| 6,284,470 | B1 | 9/2001 | Bitner et al. | |
| 6,310,199 | B1 | 10/2001 | Smith et al. | |
| 6,344,326 | B1 | 2/2002 | Nelson et al. | |
| 6,368,800 | B1 | 4/2002 | Smith et al. | |
| 6,376,194 | B2 | 4/2002 | Smith et al. | |
| 6,410,725 | B1 | 6/2002 | Scholl et al. | |
| 6,416,671 | B1 | 7/2002 | Pourfarzaneh | |
| 6,506,559 | B1 | 1/2003 | Fire | |
| 6,534,262 | B1 | 3/2003 | McKernan et al. | 435/6 |
| 6,613,895 | B1 | 9/2003 | Gautsch et al. | |
| 6,617,108 | B1 | 9/2003 | Wilson et al. | |
| 6,656,587 | B2 | 12/2003 | Johnson et al. | |
| 6,658,548 | B1 | 12/2003 | Kochar et al. | |
| 6,670,332 | B1 | 12/2003 | Wheeler | |
| 6,673,631 | B1 | 1/2004 | Tereba et al. | 436/526 |
| 6,787,307 | B1 | 9/2004 | Bitner et al. | |
| 6,804,684 | B2 | 10/2004 | Su | |
| 6,806,362 | B2 | 10/2004 | Smith et al. | |
| 6,855,499 | B1 | 2/2005 | Nargessi | 435/6 |
| 6,914,137 | B2 | 7/2005 | Baker | |
| 6,919,175 | B1 | 7/2005 | Bienhaus et al. | |
| 6,992,182 | B1 | 1/2006 | Muller et al. | |
| 7,078,224 | B1 | 7/2006 | Bitner et al. | |
| 7,208,269 | B2 | 4/2007 | Bavykin | |
| 7,264,927 | B2 | 9/2007 | Nargessi et al. | |
| 7,601,491 | B2 | 10/2009 | Collis et al. | |
| 7,727,727 | B2 | 6/2010 | Collis et al. | |
| 8,030,034 | B2 * | 10/2011 | Bitner et al. | 435/91.5 |
| 8,039,613 | B2 * | 10/2011 | Bitner | 536/25.41 |
| 2002/0004111 | A1 | 1/2002 | Matsubara et al. | |
| 2002/0162797 | A1 | 11/2002 | Johnson et al. | |
| 2002/0165388 | A1 | 11/2002 | Bavykin et al. | |
| 2003/0013112 | A1 | 1/2003 | Sprenger | |
| 2003/0096366 | A1 | 5/2003 | Knudsen | |
| 2003/0138828 | A1 | 7/2003 | Bost et al. | |
| 2004/0018559 | A1 | 1/2004 | Lau et al. | |
| 2004/0023273 | A1 | 2/2004 | Puget et al. | |
| 2004/0086930 | A1 | 5/2004 | Tereba et al. | |
| 2004/0137449 | A1 | 7/2004 | Nargessi | |
| 2004/0180445 | A1 | 9/2004 | Domanico et al. | |
| 2004/0258570 | A1 | 12/2004 | Beebe et al. | |
| 2005/0059024 | A1 | 3/2005 | Conrad | |
| 2005/0079535 | A1 | 4/2005 | Kirchgesser et al. | |
| 2005/0214926 | A1 | 9/2005 | Zielenski et al. | |
| 2005/0260625 | A1 | 11/2005 | Wang | |
| 2005/0282202 | A1 | 12/2005 | Brolaski et al. | |
| 2006/0240448 | A1 | 10/2006 | Bitner et al. | |
| 2007/0015191 | A1 | 1/2007 | Bitner et al. | |
| 2007/0087385 | A1 | 4/2007 | Muller-Schulte | |
| 2007/0172855 | A1 | 7/2007 | Bitner et al. | 435/6 |
| 2007/0249821 | A1 | 10/2007 | Bitner et al. | |
| 2009/0088560 | A1 | 4/2009 | Shen | |
| 2011/0054161 | A1 | 3/2011 | Bitner et al. | |

FOREIGN PATENT DOCUMENTS

| | | |
|---|---|---|
| CA | 2223821 | 6/1996 |
| DE | 3935098 | 4/1991 |
| DE | 4307262 | 9/1994 |
| DE | 4333805 | 3/1995 |
| DE | 19512368 | 10/1996 |
| EP | 0391608 | 10/1990 |
| EP | 0581651 | 2/1994 |
| EP | 0837871 | 6/1996 |
| EP | 0741141 | 11/1996 |
| EP | 0757106 | 2/1997 |
| EP | 0875271 | 11/1998 |
| EP | 0992583 | 4/2000 |
| EP | 1479769 | 11/2004 |
| GB | 2074892 | 11/1981 |
| JP | 62151752 | 7/1987 |
| JP | 62-190466 | 8/1987 |
| JP | 62235207 | 10/1987 |
| JP | 02-289598 | 11/1990 |
| JP | 02289596 | 11/1990 |
| JP | 03-101689 | 4/1991 |
| JP | 6126635 | 5/1994 |
| JP | 07-059572 | 3/1995 |
| JP | 07235407 | 9/1995 |
| JP | 0919292 | 1/1997 |
| JP | 9327290 | 12/1997 |
| JP | 9327291 | 12/1997 |
| JP | 10316696 | 12/1998 |
| JP | 11-92494 | 4/1999 |
| WO | WO 83/03363 | 10/1983 |
| WO | WO 86/05815 | 10/1986 |
| WO | WO 91/05606 | 5/1991 |
| WO | WO 91/12079 | 8/1991 |
| WO | WO 93/10162 | 5/1993 |
| WO | WO 95/06652 | 3/1995 |
| WO | WO 95/21177 | 8/1995 |
| WO | WO 95/21179 | 8/1995 |
| WO | WO 96/03653 | 2/1996 |
| WO | WO 96/09379 | 3/1996 |
| WO | WO 96/16186 | 5/1996 |
| WO | WO 96/31781 | 10/1996 |
| WO | WO 96/36706 | 11/1996 |
| WO | WO 96/41811 | 12/1996 |
| WO | WO 97/08547 | 3/1997 |
| WO | WO 97/29825 | 8/1997 |
| WO | WO 97/30152 | 8/1997 |
| WO | WO 97/32893 | 9/1997 |
| WO | WO 98/31461 | 7/1998 |
| WO | WO 98/31840 | 7/1998 |
| WO | WO 99/36359 | 7/1999 |
| WO | WO 99/54340 | 10/1999 |
| WO | WO 00/69872 | 11/2000 |
| WO | WO 00/70040 | 11/2000 |
| WO | WO 00/70041 | 11/2000 |
| WO | WO 01/62976 | 8/2001 |
| WO | WO 02/09125 | 1/2002 |
| WO | WO 02/38758 | 5/2002 |
| WO | WO 02/066993 | 8/2002 |
| WO | WO 02/087871 | 11/2002 |
| WO | WO 03/033739 | 4/2003 |
| WO | WO 03/040687 | 5/2003 |
| WO | WO 03/046146 | 6/2003 |
| WO | WO 03/082892 | 10/2003 |
| WO | WO 2004/096984 | 11/2004 |

| WO | WO 2004/108741 | 12/2004 |
| WO | WO 2004/108925 | 12/2004 |
| WO | WO 2005/052581 | 6/2005 |
| WO | WO 2007/005613 | 1/2007 |
| WO | WO 2007/070381 | 6/2007 |
| WO | WO 2007/103485 | 9/2007 |
| WO | WO 2008/112015 | 9/2008 |
| WO | WO 2008/127356 | 10/2008 |
| WO | WO 2011/026027 | 3/2011 |
| WO | WO 2011/026028 | 3/2011 |

OTHER PUBLICATIONS

Aida, Y. et al., "Removal of endotoxin from protein solutions by phase separation using Triton X-114," J. Immunol. Methods (1990) 132:191-195.

Anspach, F.B. "High performance liquid affinity chromatography with phenylboronic acid, benzamidine, tri-L-alanine, and concanavalin A immobilized on 3-isothiocyanatopropytriethoxysilane-activated nonporous monodisperse silicas," Anal. Biochem. (1989) 1797:171-181.

Anspach, F.B. et al., "Removal of endotoxins by affinity sorbents," J. Chrom. A (1995) 711:81-92.

Astell et al., "Thermal elution of complementary sequences of nucleic acids from cellulose columns with covalently attached oligonucleotides of known length and sequence," J. Biol. Chem. (1971) 248:1944-1946.

Ausubel et al., eds. Chapter 2 (DNA) and Chapter 4 (RNA) of Current Protocols in Molecular Biology, Wiley-Interscience, New York (1993).

Ausubel et al., eds., Chapter 2 (DNA) and Chapter 4 (RNA) of Current Protocols in Molecular Biology, Wiley-Interscience, New York (1987).

Ausubel, F.M. et al., Short Protocols in Molecular Biology, Third Edition, John Wiley & Sons, Inc. (1997) p. 9-52.

Biocontrol Network, "Perma-guard diatomaceous earth," http://www.biconet.com (1998) 5 pages.

Bischoff, R. et al., "Chemically synthesized hydrophobic anion-exchange high-performance liquid chromatography supports used for oligonucleotide resolution by mixed mode chromatography," J. Chromatog. (1983) 270:117-126.

Bischoff, R. et al., "Nucleic acid resolution by mixed-mode chromatography," J. Chromatog (1984) 296:329-337.

Bitner R. et al., "Automation of DNA extraction from food and plants using MagneSil™ paramagnetic particles," Proceedings of SPIE V. 4264 (2001). Submitted Jan. 2001, Genomics & Proteomics Technologies, pp. 9-16.

Bitner, R et al., "Use of MagneSil paramagnetic particles for plasmid purification, PCR cleanup and purification of dideoxy and big dye DNA sequencing reactions," Advances in Nucleic Acid and Protein Analyses, Manipulation and Sequencing, Proceedings of SPIE (2000) 3926:126-133.

Boom, R. et al., "Rapid and simple method for purification of nucleic acids," J. Clin. Microbiol. (1990) 28:495-503.

Brinker, C.J. et al., "Sol gel science: the physics and chemistry of sol gel processing," Academic Press Inc. (1990).

Brisco, P. et al., "Use of a 96 well format for small scale mRNA isolation and cDNA synthesis,"*Promega Notes Magazine*, No. 52, pp. 8-13 (1995).

Brown et al., "Anion-cation separations on a mixed bed alumina-sillica column," J. Chromatog. (1989) 466(1):291-300.

Brummelkamp et al., "A system for stable expression of short interfering RNAs in mammalian cells," Science (2002) 296:550-553.

Burke, P., "PolyATtract® mRNA isolation systems," *Promega Notes Magazine*, No. 56, p. 27-29 (1996).

Caplen, N. et al., "Specific inhibition of gene expression by small double-stranded RNAs in invertebrate and vertebrate systems," Proc. Natl. Acad. Sci. USA (2001) 98(17):9742-9747.

Chen et al., Anal. Biochem. (1980) 101:339-341.

Controlled Pore Glass Products, CPG, Inc., Online, http://www.cpg-biotech.com (2002).

Cotten, M. et al., "Lipopolysaccharide is a frequent contaminant of plasmid DNA preparations and can be toxic to primary human cells in the presence of adenovirus," Gene Therapy (1994) 1:239-246.

Creswell, D., et al., "Increasing yield with the Wizard® PureFection Plasmid DNA Purification System," *Promega Notes Magazine*, No. 73 pp. 17-19 (1999)).

Crowther, J.B. et al., "High-performance liquid chromatographic separation of oligonucleotides and other nucleic acid constituents on multifunctional stationary phases," J. Chromatog (1983) 282:619-628.

Davies, M.J. et al., "Isolation of plasmid DNA using magnetite as a solid-phase adsorbent," Anal. Biochem. (1998) 262:92-94.

Davis, H.L. et al., "Direct gene transfer into skeletal muscle in vivo: factors affecting efficiency of transfer and stability of expression," Human Gene Ther. (1993) 4:151-159.

Edwardson, P.A.D. et al, "Separation and purification of oligonucleotides using a new bonded-phase packing material," J. Chromatog. (1991) 545:79-89.

Elbashir, S.M. et al., "Duplexes of 21-nucleotide RNAs mediate RNA interference in cultured mammalian cells," Nature (2001) 411:494-498.

Elbashir, S.M. et al., "Functional anatomy of siRNAs for mediating efficient RNAi in Drosophila melanogaster embryo lysate," EMBO J. (2001) 20(23):6877-6888.

Elbashir, S.M. et al., "RNA interference is mediated by 21- and 22-nucleotide RNAs," Genes & Dev. (2001) 15:188-200.

Ennifar, E. et al., "A crystallographic study of the binding of 13 metal ions to two related RNA duplexes," Nucl. Acids Res. (2003) 31(10):2671-2682.

Figueroa, A. et al., "High-performance immobilized-metal affinity chromatography of proteins on iminodiacetic acid silica-based bonded phases," J. Chromatog. (1986) 371:335-352.

Floyd, T.R. et al., "Mixed-mode hydrophobic ion exchange for the separation of oligonucleotides and DNA fragments using HPLC," Analytical Biochemistry (1986) 154:570-577.

Ford, The University of Edinburgh, U.K., Welcome to the Biology Teaching Organisation, see glossary definition of "lysis," web published with last update of Nov. 19, 1997, originally published at http://www.icmb.edinburgh.ac.uk.bto/glossary 3 pages.

Franklin, R.M., "Purification and properties of the replicative intermediate of the RNA bacteriophage R17," Biochem. (1966) 55:1504-1511.

Gibco BRL Products & References Guide 1997/1998, Life Technologies, "Aces 2.0+ human DNA quantitation system," pp. 19-28.

Gjerde, D.T. et al., Ion chromatography, Ch. 3, Dr. Alfred Hothig Verlag Heidelberg (1987) 2nd Edition, 3 pages.

Goldsborough, M.D. et al., "High purity plasmid DNA from anion exchange chromatography," Focus (1998) 20(3):68-69.

Greenspoon, S. et al., "Robotic extraction of mock sexual assault samples using the biomek 2000 and the DNA IQ system," Profiles in DNA (2002) 5(1).

Harkins, W.D. et al., Proceedings of the National Academy of Sciences of the United States of America (1916) 2(10):599-600, http://www.jstor.org/stable/83481.

Harris, A.B., "Solvent pH and salt concentration in rapid resolution of nucleic acid bases on cellulose layers," Biochem. Biophys. Acta (1967) 145:520-522.

Hawkins et al., "DNA purification and isolation using a solid-phase," Nucl. Acids. Res. (1994) 22(21):4543-4544.

Hirabayashi, J., "Applied slalom chromatography improved DNA separation by the use of columns developed for reversed-phase chromatography," J. Chrom. (1996) 722:135-142.

Holen, T. et al., "Positional effects of short interfering RNAs targeting the human coagulation trigger tissue factor," Nucl. Acids Res. (2002) 30(8):1757-1766.

http://seq.yeastgenome.org/vector_descrip/COMPLETE/PUC18. seq.htm, downloaded Nov. 13, 2008.

Huber, C.G. et al., "High-resolution liquid chromatography of DNA fragments on non-porous poly(styrene-divinylbenzene) particles," Nucl. Acids. Res. (1993) 21(5):1061-1066.

Jost, W. et al., "Application of a weekly basic dimethylamino-modified silica ion exchanger to the separation of oligonucleotides," J. Chromatog. (1979) 185:403-412.

Karplus, T.E. et al., "A new method for reduction of endotoxin contamination from protein solutions," J. Immunol. Met. (1987) 105:211-220.

Kephart, D., "Rapid isolation of RNA from small quantities of human whole blood for use in RT-PCR analysis," *Promega Notes Magazine*, No. 62 pp. 11-16 (1997).

Keys et al., "The use of cellulose phosphate in the extraction of free nucleotides from plant tissue," Proceedings of the Biochemical Society (1969) p. 16-17.

Kieft, J.S. et al., "Solution structure of a metal-binding site in the major groove of RNA complexed with cobalt (III) hexammine," Structure (1997) 5(5):713-721.

Kimpton et al., "Validation of highly discriminating multiplex short tandem repeat amplification systems for individual identification," Electrophoresis (1996) 17(8):1283-1293.

Kirk-Othmer Encyclopedia of Chemical Technology, vol. 21, 4th Edition, Mary Howe-Grant, Ed., John Wiley & Sons (1997) p. 1020-1023.

Kirk-Othmer Encyclopedia of Chemical Technology, vol. 6, 4th ed., John Wiley & Sons (1993) pp. 773-775.

Kleiber, J. et al., "Magnetic particles and their use for isolation of biological materials," Gen. Offen. (1996) Database CAS online AN 126:86772 9 pp. Abstract, 1 page.

Kothari et al., "RNA fractionation on modified celluloses," J. Chromatog. (1972) 73:449-462.

Kotsopoulos, S.K. et al., "Isolation of 3.5-KB fragments on magnetic solid supports," BioTechniques (1996) 20:198-200.

Krizova, J. et al., "Magnetic hydrophilic methacrylate-based polymer microspheres for genomic DNA isolation," J. Chromatog. A (2005) 1064:247-253.

Lepinski, M., "Tips for working with RNA and troubleshooting downstream applications," *Promega Notes Magazine*, No. 63 pp. 17-20 (1997).

Levison, P.R. et al., "New approaches to the isolation of DNA by ion-exchange chromatography," J. Chromat. (1998) 827(2):337-344.

Levison, P.R. et al., "Recent developments of magnetic beads for use in nucleic acid purification," J. Chromatography A (1998) 816:107-111.

Lin, Z. et al., "Protocol for genomic DNA preparation from fresh or frozen serum for PCR amplification," BioTechniques (2000) 29:460-466.

Little, E.L. et al., "Sequential multimodal elution for pseudomultidimensional liquid chromatography on a single column," Anal. Chem. (1991) 63:33-44.

Liu, S. et al., "Removal of endotoxin from recombinant protein preparations," Clin. Biochem. (1997) 30(6):455-463.

Livage, J. et al. "Encapsulation of biomolecules in silica gels," J. Phys.: Condens. Matter (2001) 13:R673-691.

Maa, Y.F. et al., "Rapid high-performance liquid chromatography of nucleic acids with polystyrene-based micropellicular anion exchangers," J. Chromatog. (1990) 508:61-73.

Macherey-Nagel, homepage on the Internet on Jun. 12, 1998 at http://www.machrey-nagel.com, 3 pages.

Makowski et al., "Amplification of guthrie card DNA: effect of guanidine thiocyanate on binding of nature whole blood PCR inhibitors," J. Clin. Lab. Anal. (1997) 11:87-93.

Manthorpe, M. et al., "Gene therapy by intramuscular injection of plasmid DNA: studies on firefly luciferase gene expression in mice," Human Gene Therapy (1993) 4:419-431.

Mariani et al., "Development of novel, rapid processing protocol for polymerase chain reaction-based detection of bacterial infections in synovial fluids" Mol. Biotech. (1995) 4(3):227-237.

Marko, M.A. et al., "A procedure for the large-scale isolation of highly purified plasmic DNA using alkaline extraction and binding to glass powder," Anal. Biochem. (1982) 121:382-287.

Marvin, H.J.P. et al., "Release of outer membrane fragments from wild-type *Escherichia coli* and from several *E coli* lipopolysaccharide mutants by EDTA and heat shock treatments," J. Bacter. (1989) 171(10):5262-5267.

Matsubara et al., "Dried blood spot on filter paper as a source of mRNA," Nucl. Acids Res. (1992) 20(8):1998.

Matsubara et al., Wizard Minipreps Dna Purification Systems, Promega Corporation (Dec. 1994) 1-4.

McCormick, R.M. et al., "A solid-phase extraction procedure for DNA purification," Anal. Biochem. (1989) 181:66-74.

McElroy et al., "QSAR and classification of murine and human soluble epoxide hydrolase inhibition by urea-like compounds," J. Med. Chem. (2003) 46(6):1066-1080.

McLaughlin, L., "Mixed-mode chromatography of nucleic acids," Chem. Rev. (1989) 89:309-319.

Melzak, K.A. et al., "Driving forces for DNA adsorption to silica in perchlorate solutions," J. Colloid Interface Sci. (1996) 181:635-644.

Molvig, J. et al., "Removal of endotoxin from culture media by a polymyxin B sepharose column," Scand. J. Immunol. (1987) 26:611-619.

Montbriand, P.M. et al., "Improved method for the removal of endotoxin from DNA," J. Biotech. (1996) 44:43-46.

Morrison, D.C. et al., "Endotoxin and disease mechanisms," Ann. Rev. Med. (1987) 38:417-432.

Mrazek, F. et al., "Processing of MRNA from human leukocytes by biomagnetical separation: comparison with current methods of RNA isolation," Acta Univ. Palacki. Olomuc. Fac. Med. (1999) 142:23-28.

Murphy, J.C. et al., "RNA isolation and fractionation with compaction agents," Anal. Biochem. (2001) 295:143-148.

Neri, B.P., et al., "Transferring automation for large-scale development and production of invader SNP assays," Abstract, Bios (2000) 2 pages.

Northrop, D.M. et al., "Preparation and evaluation of a bimodal size-exclusion chromatography column containing a mixture of two silicas of different pore diameter," Anal. Chem. (1991) 63:1350-1354.

Osorio, C.R. et al., "Characterization of the 23S and 5S rRNA genes and 23S-5S intergenic spacer region (ITS-2) of *Photobacterium damselae*," Dis. Squat. Org. (2004) 61:33-39.

PerSeptive Diagnostics Product Guide for BioMag® MINI-PPEP DNA Purification Kit (Catalog No. 8-MB4008K) Feb. 27, 1995 (4 pages).

Pourfarzaneh et al., "The use of magnetizable particles in solid phase immunoassay," Methods of Biochem. Anal. (1982) 28:267-295.

Promega Corporation—1994-95 Biologic Research Products Catalog, front cover, table of contents, pp. 155-157 (1994) PolyATtract® mRNA Isolation Systems, PolyATtract® System 1000 Magnetic Separation Stand & MagneSphere™ Technology Magnetic Separation Stand, 5 pages.

Promega Corporation—"Material Safety Data Sheet: Wizard SV96 Neutralization Solution" http://www.promega.com/msds/uk/ukmsds\A148.htm, (Jul. 3, 2002) *Box 2 (composition/data on components):guanidinium chloride*, 1-5 pages.

Promega Corporation—"Wizard SV96 Plasmid DNA Purification System" (1999) Retrieved from the Internet on Sep. 5, 2007 (http://www.promega.co.jp/jp/jp_tech/jp_manuals/wsv96.pdf) pp. 1-9.

Promega Corporation—"Frequently asked questions of Promega's Technical Services Department," *Promega Notes*, No. 71, pp. 24-26 (1999).

Promega Corporation—1990-91 Product Catalogue, front and back cover, pp. 121-122 (1990) (PolyATtract™ mRNA Isolation Systems) 4 pages.

Promega Corporation—1991-92 Product Catalogue, front cover, first page of table of contents, pp. 192 and 348 (1991) (PolyATtract™ mRNA Isolation Systems & MagneSphere™ Technology Magnetic Separation Stand) 4 pages.

Promega Corporation—1992-93 Biologic Research Products Catalogue, front and back cover, first page of table of contents, pp. 161-163 (1992) (PolyATtract® mRNA Isolation Systems, PolyATtract® System 1000 Magnetic Separation Stand & MagneSphere™ Technology Magnetic Separation Stand) 6 pages.

Promega Corporation—1993-94 Product Catalog, front and back cover, first page of table of contents, pp. 149-151 (1993) (PolyATtract® mRNA Isolation Systems, PolyATtract® System 1000 Magnetic Separation Stand & MagneSphere™ Technology Magnetic Separation Stand) 5 pages.

Promega Corporation—1996 Biologic Research Products Catalog, front cover, table of contents, pp. 158-161 (1995) (PolyATtract® mRNA Isolation Systems, PolyATtract® System 1000 Magnetic Separation Stan, PolyATtract® Series 9600™ Multi-Magnet & MagneSphere™ Technology Magnetic Separation Stand) 6 pages.

Promega Corporation—1997 Biologic Research Products Catalog, front cover, table of contents, pp. 187-188 (1996) (PolyATtract® mRNA Isolation Systems, PolyATtract® System 1000 Magnetic Separation Stand, PolyATtract® Series 9600™ Multi-Magnet & MagneSphere™ Technology Magnetic Separation Stand) 5 pages.
Promega Corporation—1998 Biologic Research Products Catalog, cover and pp. 182-183 and 199-200, 5 pages.
Promega Corporation—1998 Biologic Research Products Catalog, front cover, table of contents, pp. 196-200 (1997) (PolyATtract® mRNA Isolation Systems, PolyATtract® System 1000 Magnetic Separation Stand, PolyATtract® Series 9600™ Multi-Magnet & MagneSphere™ Technology Magnetic Separation Stand), 7 pages.
Promega Corporation—1999 Life Science Catalog, front cover, table of contents, pp. 9.4, 9.19-9.22 and 10.17 (1998) (Wizard® PureFection Plasmid DNA Purification System, PolyATtract® mRNA Isolation Systems, PolyATtract® System 1000 Magnetic Separation Stand, PolyATtract® Series 9600™ Multi-Magnet & MagneSphere™ Technology Magnetic Separation Stand), 8 pages.
Promega Corporation—2000 Life Science Catalog, front cover, table of contents, pp. 2.4 and 2.12-2.14 (1999) (Wizard PureFection Plasmid DNA Purification System, PolyATtract mRNA Isolation Systems, PolyATtract System 1000 Magnetic Separation Stand, PolyATtract Series 9600 Multi-Magnet and MagneSphere Technology Magnetic Separation Stand), 6 pages.
Promega Corporation—Higher Throughput Solutions Brochure, BR094, (Jun. 2000) 6 pages.
Promega Corporation—MagneSphere® Magnetic Separation Products Technical Bulletin, TB246 (Nov. 1996) 1-10.
Promega Corporation—MagneSpheree Magnetic Separation Products Technical Bulletin, TB246 (revised Mar. 2000) 1-12.
Promega Corporation—Nucleic Acid Purification Systems Brochure, BR081 (Feb. 1999) 11 pages.
Promega Corporation—PolyATtract® mRNA Isolation System Technical Manual, TM021 (Revised Feb. 2000) 1-12.
Promega Corporation—PolyATtract® mRNA Isolation System Technical Manual, TM021 (Revised Apr. 1995)1-11.
Promega Corporation—PolyATtract® mRNA Isolation System Technical Manual, TM021 (Revised May 2001) 1-12.
Promega Corporation—PolyATtract® mRNA Isolation System Technical Manual, TM021 (Revised Aug. 1998) 1-16.
Promega Corporation—PolyATtract® System 1000 Technical Manual, TM228 (Dec. 1992) 1-19.
Promega Corporation—PolyATtract® System 1000 Technical Manual, TM228 (Revised May 2001) 1-19.
Promega Corporation—PolyATtract® System 1000 Technical Manual, TM228 (Revised Dec. 1999) 1-24.
Promega Corporation—PolyATtract® System 1000 Technical Manual, TM228 (Revised Feb. 2000) 1-23.
Promega Corporation—PolyATtract® System 1000 Technical Manual, TM228 (Revised Feb. 1997) 1-19.
Promega Corporation—PolyATtract® System 1000 Technical Manual, TM228 (Revised Mar. 1995) 1-18.
Promega Corporation—PolyATtract® System 1000 Technical Manual, TM228 (Revised Apr. 1999) 1-23.
Promega Corporation—PolyATtract® System 1000 Technical Manual, TM228 (Revised Jun. 1997) 1-19.
Promega Corporation—PolyATtract® System 1000 Technical Manual, TM228 (Revised Jun. 1998) 1-23.
Promega Corporation—Technical Bulletin No. 202, "Wizard Plus Series 9600 DNA Purification System" (Sep. 1998) 18 pages.
Promega Corporation—Technical Bulletin No. 225, "Wizard Plus SV Minipreps DNA Purification System" (Sep. 1999) 14 pages.
Promega Corporation—Technical Bulletin No. 48, "SV Total RNA Isolation System" (1998), 28 pages.
Promega Corporation—Wizard ® MagneSil™ Plasmid Purification System, TB286 (Nov. 1) pp. 1-12.
Promega Corporation—Wizard MagneSil Tfx™ System, Technical Bulleting TB314, first printing (Oct. 2002) pp. 1-9.
Promega Corporation—WIZARD® MagneSil™ Plasmid Purification System, Technical Bulletin TB286, First Printing (Feb. 2001) pp. 1-11.
Promega Corporation—Wizard® Magnetic DNA Purification System for Food Technical Bulletin, TB284 (Aug. 2000) (PolyATtract® System 1000 Magnetic Separation Stand, Cat. #Z5410), pp. 1-11.

Promega Corporation—Wizard® Magnetic DNA Purification System for Food Technical Bulletin, TB284 (Revised Mar. 2001) (PolyATtract® System 1000 Magnetic Separation Stand, Cat. #Z5410), pp. 1-13.
Promega Corporation—Wizard® Magnetic DNA Purification System for Food Technical Bulletin, TB284 (Revised May 2001) (PolyATtract® System 1000 Magnetic Separation Stand, Cat. #Z5410), pp. 1-14.
Promega Corporation—Wizard® PureFection Plasmid DNA Purification Brochure, BR076 (Feb. 1999), pp. 1-9.
Promega Corporation—Wizard® PureFection Plasmid DNA Purification System Technical Bulletin, TB259 (Oct. 1998) pp. 1-14.
Promega Corporation—Wizard® PureFection Plasmid DNA Purification System Technical Bulletin, TB259 (Feb. 1999) pp. 1-14.
Promega Corporation—Wizard® PureFection Plasmid DNA Purification System, Neural Notes, vol. 4, Issue 2 (1998) p. 14.
Promega Corporation—Wizard® Purification Systems Brochure, BR072 (Jul. 1998) pp. 1-7.
Promega DNA IQ System-Database Protocol, TB 297, revised Jun. 2002.
Promega DNA IQ System-Small Sample Casework Protocol, TB296, revised Jun. 2002.
Promega, Technical Bulletin No. 117 "Wizard Miniprep" (Dec. 1994).
QIAGEN Plasmid Purification Handbook (Jan. 1997) 67 pages.
Quantiblot, Quantiblot Human DNA Quantitation System, PE Applied Biosystems, Feb. 5, 1996, p. 1-5 (http://www.pebio.com/fo/773503/773503.html).
Rassi, Z.E. et al., "Tandem columns and mixed-bed columns in high-performance liquid chromatography of proteins," J. Chrom. (1986) 359:255-264.
Rudi, K. et al., "Rapid, universal method to isolate PCR-ready DNA using magneteic beads," BioTechniques (1997) 22:506-511.
Sambrook et al., Molecular Cloning a Laboratory Manual, 2nd edition, Cold Spring Harbor Laboratory Press (1989) p. 1.25-1.28.
Sambrook, J. et al., "Extraction and purification of plasmid DNA," Molecular Cloning, a Laboratory Manual, Second Edition, Cold Harbor Laboratory Press (1998) 1.21-1.45.
Sambrook, J. et al., Molecular Cloning a Laboratory Manual, 2nd edition, Cold Spring Harbor Laboratory Press (1989) p. 2.22 and filtration system reference.
Scott, D.L. Jr. et al., "The use of biomagnetic separation to recover DNA suitable for PCR from claviceps species," Lett. Appl. Microbiol. (2000) 31:95-99.
Shiels, G, et al., MagneSil™ C'este Magnifique!, Promega Notes 79 (2001), 3 pages.
Shih et al., "Chemical linkage of nucleic acids to neutral and phosphorylated cellulose powders and isolation of specific sequences by affinity chromatography," Biochem. (1974) 13:3411-3418.
Sigma-Aldrich 1997 Catalog, cover and p. 448.
Smith, D. et al., "Automated purification of plasmid DNA using paramagnetic particles," Jala V. 8(3) pp. 50-54 (Jun. 2003).
Sparkes et al., "The validaticin of a 7-locus multiplex STR test for use in forensic casework," Int. J. Legal Med. (1996) 109:195-204.
Su et al., "Cellulose as a matrix for nucleic acid purification," Anal. Biochem. (1999) 267:415-418.
Taylor, J.I. et al., "Application of magnetite and silica-magnetite composites to the isolation of genomic DNA," J. Chromatography A (2000) 890:159-166.
Tereba et al., "Simultaneous purification and quantitation of DNA from liquid blood and bloodstains," submitted on Mar. 1, 1999 to the International Association of Forensics Sciences (IAFS) Meeting, Aug. 1999.
Tuschl, T. et al., "Small interfering RNAs: a revolutionary tool for the analysis of gene function and gene therapy," A Role for siRNAs in Genetic Therapy, Molecular Interventions (2002) 2(3):158-167.
Vogelstein et al., "Preparative and analytical purification of DNA from Agarose," PNAS (1979) 76(2):615-619.
Waterborg et al., "Efficient large-scale purification of restriction fragments by solute-displacement ion-exchange HPLC," Nucleic Acids Res. (1993) 21(12):2913-2915.
Weber et al., "Effects of lipopolysaccharide on transfection efficiency in eukaryotic cells," Biotechniques (1995) 19(6):930-940.

Weith et al., "Synthesis of cellulose derivatives containing the dihydroxyboryl group and a stufy of their capacity to form specific complexes with sugars and nucleic acid components," Biochem. (1970) 9:4396-4401.

Wheatley, J.B., "Multiple ligand applications in high-performance immunoaffinity chromatography," J. Chromatogr. (1992) 603:273.

White, D., et al., "Automated purification of transfection-grade plasmid DNA using Wizard MagneSil Tfx System," JALA, v. 8(4), pp. 50-53 (2003).

White, D., et al., "Be a "Wizafd" at transfection," Promega Notes 83 (2003) pp. 18-20.

White, D., et al., "Cells to Gels: Automated purification of plasmid DNA directly from bacterial culture with normalization," Promega Notes, No. 85 (2003) pp. 28-30.

White, D., et al., MagneSil™ paramagnetic particles: Novel magnetics for DNA purification, Promega Notes, No. 69 (1998) pp. 12-15.

White, D., et al., Wizard® PureFection plasmid DNA purification system: The new standard in isolating transfection grade plasmid DNA, Promega Notes, No. 68 (1998) pp. 2-9.

Wicks et al., "Bacterial lipopolysaccharide copurifies with plasmid DNA: implications for animal models and human gene therapy," Human Gene Therapy (1995) 6:317-323.

Wirth, M.J. et al., "Mixed self-assembled monolayers in chemical separations," Science (1997) 275:44-47.

Wolfe, K.A. et al., "Toward a microchip-based solid-phase extraction method for isolation of nucleic acids," Electrophoresis (2002) 23(5):727-733.

Zhang, Y-P. et al., "A small-scale procedure for extracting nucleic acids from woody plants infected with various phytopathogens for PCR assay," J. Virol. Meth. (1998) 71:45-50.

International Search Report and Written Opinion for Application No. PCT/US2010/047137 dated Dec. 9, 2010 (8 pages).

International Search Report and Written Opinion for Application No. PCT/US2010/047139 dated Jan. 20, 2011 (9 pages).

United States Patent Office Notice of Allowance for U.S. Appl. No. 12/549,806 dated May 16, 2011 (6 pages).

United States Patent Office Action Notice of Allowance for U.S. Appl. No. 12/549,806 dated Jun. 9, 2011 (4 pages).

Mrazek et al., *Acta Univ. Palacki. Olomuc., Fac. Med.* 142:23-28 (1999).

Lin et al., *BioTechniques*, 29:460-466 (2000).

Scott Jr. et al., *Lett. Appl. Microbiol.*, 31:95-99 (2000).

Ahn et al., *BioTechniques*, 29:466-468 (2000).

Taylor et al., *J. Chromatography A*, 890:159-166 (2000).

United States Patent Office Supplemental Notice of Allowability for U.S. Appl. No. 12/549,806 dated Sep. 15, 2011 (6 pages).

Lin et al., "Chromatography of nucleic acids on polynucleotide-coated kieselguhr," Biochim. Et Biophys. Acta—Nucl. Acids and Prot Synth. (1970) 217(2):1 page, abstract.

* cited by examiner

METHODS OF OPTIMAL PURIFICATION OF NUCLEIC ACIDS AND KIT FOR USE IN PERFORMING SUCH METHODS

FIELD OF THE INVENTION

This invention relates to methods of optimally purifying nucleic acids, and also to a kit for use in performing such methods.

BACKGROUND OF THE INVENTION

The purification of deoxyribonucleic acid (DNA) or ribonucleic acid (RNA) plays an important role in scientific procedures. There are a number of known methods of purifying single- and double-stranded DNA or RNA contained in biological fluids such as human blood, serum, and cultured cells, as well as plants, animal and human tissues, and other specimens. However, such methods can result in very low yields and do not always work well when trying to extract small amounts of DNA from large samples. Known methods are described in, for example, Nargessi, U.S. Pat. No. 6,855,499 (2005); Tereba et al., U.S. Pat. No. 6,673,631 (2004); McKernan et al., U.S. Pat. No. 6,534,262 (2003); Taylor et al., *J. Chromatography A*, 890:159-166 (2000); Ahn et al., *BioTechniques*, 29:466-468 (2000); Scott Jr. et al., *Lett. Appl. Microbiol.*, 31:95-99 (2000); Lin et al., *BioTechniques*, 29:460-466 (2000); Smith et al., U.S. Pat. No. 6,027,945 (2000); Mrazek et al., *Acta Univ. Palacki. Olomuc., Fac. Med.* 142:23-28 (1999); Hawkins, U.S. Pat. No. 5,898,071 (1999); and Hawkins, U.S. Pat. No. 5,705,628 (1998).

SUMMARY OF THE INVENTION

This invention is an improvement over the known methods described in the aforementioned literature.

In one aspect, the invention relates to a method of purifying a defined quantity of nucleic acid, which is contained in a medium, such as whole blood, plasma, or tissue cell cultures obtained from humans, plants, or animals. The method includes steps of (a) combining the medium containing nucleic acid with a definable amount of a binding matrix capable of reversibly binding nucleic acid, and a formulation, the formulation being sufficient to cause the nucleic acid to separate from its in vivo cellular environment and to bind to the binding matrix, under a first set of binding conditions, wherein the amount of nucleic acid bound to the binding matrix is essentially independent of the amount of surface area of the definable amount of the binding matrix, (b) separating the binding matrix with nucleic acid bound thereto from substantially the rest of the combined medium and formulation, (c) eluting the nucleic acid from the binding matrix, thereby obtaining nucleic acid in a substantially purified form, (d) using the definable amount of binding matrix used in step (a), the amount of nucleic acid provided in step (c) being in excess of the binding capacity of the binding matrix under a second set of binding conditions, wherein the amount of nucleic acid bound to the definable amount of binding matrix is essentially dependent on the amount of surface area of the definable amount of the binding matrix, (e) forming a complex of the binding matrix and the nucleic acid by combining the binding matrix and the medium, under a second set of binding conditions, wherein the amount of nucleic acid bound to the definable amount of binding matrix is essentially dependent on the amount of surface area of the definable amount of the binding matrix, (f) removing the complex with the nucleic acid from the medium, and (g) separating the nucleic acid of step (f) from the complex, whereby a defined quantity of nucleic acid is obtained.

The nucleic acid may be DNA, RNA, or a combination of DNA and RNA, and is considered to be in a "substantially purified form" when the nucleic acid has been separated from its in vivo cellular environment and obtained in a form that is useful in one or more scientific procedures, such as the isolation of genetic material, polymerase chain reactions, electrophoresis, sequencing, and cloning, among others.

The formulations used in the foregoing method can contain an amount of proteinase K, 1-thioglycerol, lysis solutions, polyethylene glycol, NaCl, 1,2 propane diol, alcohol, CHAPS (3-[(3-cholamidopropyl)dimethylammonio]-1-propanesulfonate, available from SIGMA-ALDRICH™, catalog item C3023), TERGITOL™ type NP-9 (26-(4-nonylphenoxy)-3,6,9,12,15,18,21,24-octaoxahexacosan-1-ol available from SIGMA-ALDRICH™, catalog item np9), TRITON™ X-100 (4-(1,1,3,3-tetramethylbutyl)phenyl-polyethylene glycol, available from Thermo Scientific, Waltham, Mass., catalog item BP151), guanidine thiocyanate and an amount of (i) acetamide, (ii) one or more acetamide derivatives, or (iii) a combination of acetamide and one or more acetamide derivatives. Preferred acetamide derivatives include methylacetamide and dimethylacetamide. Herein, guanidine thiocyanate is sometimes referred to as "GTC," and the combination of guanidine thiocyanate with acetamide and/or one or more acetamide derivatives is sometimes referred to as "GTC-A."

In a preferred embodiment of the foregoing method, the first set of binding conditions comprises a concentration of polyethylene glycol from approximately 5% (weight to volume) to 12% (weight to volume), and the concentration of NaCl is from approximately 0.5M to 1.5M to facilitate binding of nucleic acid to the binding matrix, and the second set of binding conditions comprises GTC-A chemistries to facilitate binding of the defined quantity of nucleic acid to the binding matrix.

In another preferred embodiment, for the purification of RNA or a combination of DNA and RNA, the first binding formulation may comprise 1,2 propane diol and a salt (e.g., NaCl, sodium citrate), or a combination of 1,2 propane diol, salt and an alcohol.

If GTC-A is used in the second binding condition of the above method, the respective amounts of GTC and acetamide and/or acetamide derivative(s) present in the formulation are sufficient to cause the at least one nucleic acid to separate from its in vivo cellular environment and to bind to the binding matrix. Preferably, the concentration of GTC in the formulation is from approximately 2.6M to approximately 4.3M. Preferably, the concentration of acetamide and/or acetamide derivative(s) in the formulation is from approximately 5.0M to approximately 7.0M.

Any of a number of known binding matrices can be used in the foregoing method, depending on the type of nucleic acid sought to be purified. Those skilled in the art will be able to select a binding matrix that is compatible with the DNA, RNA or a combination of DNA and RNA. Examples of suitable binding matrices include, but are not limited to, paramagnetic cellulose particles, paramagnetic carboxy-cellulose particles, paramagnetic zeolite particles, paramagnetic silica particles, cellulose membranes, silica membranes, nylon membrane columns, PVDF membrane columns, polypropylene columns, HIGH PURE™ spin columns (available from Roche Diagnostics item 1 828 665), chemically modified cellulosic materials comprising vicinal diols, zeolite, and nylon.

Optionally, one or more additional ingredients can be combined with the medium, the binding matrix, and the formulation. For example, one or more enzymes which aid in the degradation and lysis of cellular structure can be used to facilitate the separation of nucleic acids such as DNA from their mediums. Examples of suitable additional ingredients include, but are not limited to, proteinase K (available from Promega, Madison, Wis., catalog item V3021), 1-thioglycerol (1-TG) (available from SIGMA-ALDRICH™, St. Louis, Mo., catalog item M2172), lysis solutions, CHAPS (available from SIGMA-ALDRICH™, catalog item C3023), TERGITOL™ type NP-9 (available from SIGMA-ALDRICH™, catalog item np9), and TRITON® X-100 (available from Thermo Scientific, Waltham, Mass., catalog item BP151). How these additional ingredients are employed is not critical. For example, they can be incorporated in the formulation, or they can be added to the medium either before or after the medium is combined with the binding matrix and/or the formulation.

In another aspect, the invention relates to a method as described above, except that the separation and eluting steps, (f) and (g), are not necessarily required, although such steps are not excluded. Thus, the binding matrix with the nucleic acid bound thereto can form a complex of the binding matrix and the nucleic acid without separating from the binding matrix.

In yet another aspect, the invention relates to a kit for use in purifying nucleic acid and/or binding nucleic acid to a binding matrix. The kit includes a binding matrix and formulations as described above. Preferably, the ratio of binding matrix to formulation in the kit is within the range of from 1:400 to 1:1, by volume. The preferred amount of binding matrix is dependent on the preferred predetermined amount of nucleic acid that is desired using the second binding condition. The ratio of binding matrix to formulation can be varied within or outside of this preferred range, depending on, among other things, the nucleic acid(s) of interest and the type of binding matrix employed.

DETAILED DESCRIPTION OF THE PREFERRED EMBODIMENTS

Figure 1:
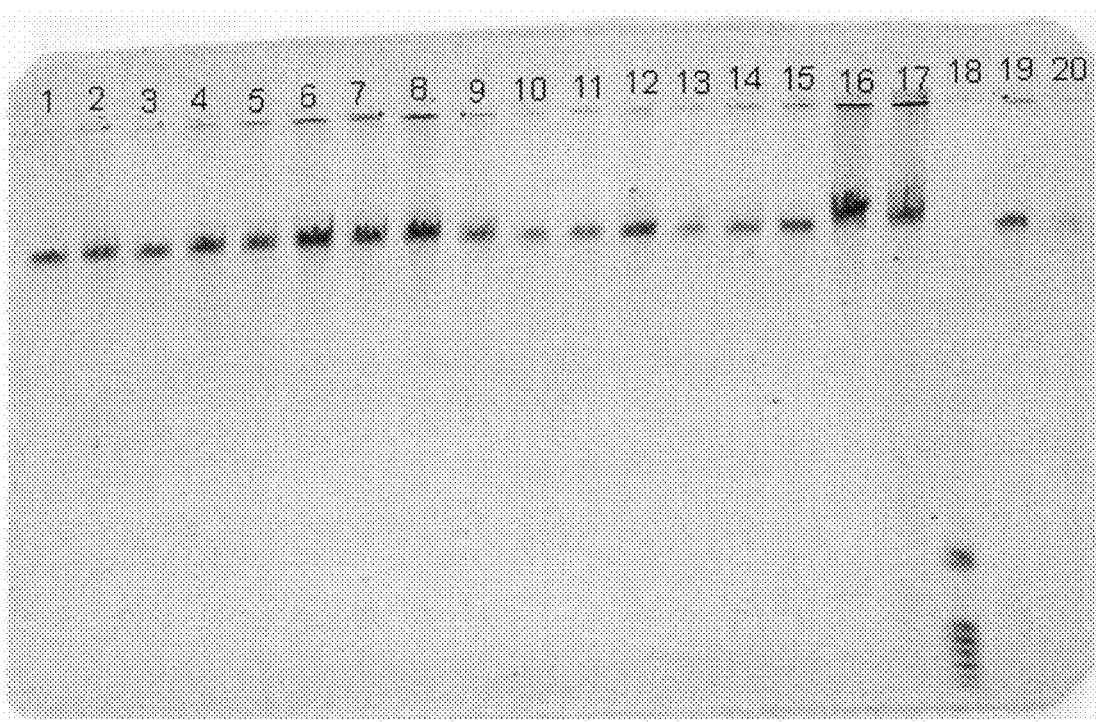
FIG. 1 is a photograph showing the results of an electrophoresis analysis performed in accordance with Example 1, described below.

The following are non-limiting examples of preferred implementations of this invention. Throughout this specification, all volumes, pH levels, and concentrations are at room temperature unless stated otherwise. Specific temperatures, concentrations, and methods are only examples of preferred embodiments and should not be considered limiting in any way. For example, the words vortexing and mixing can be used interchangeably to mean combining the contents into equal or balanced parts.

Nucleic Acids

The nucleic acid capable of being purified using the present invention includes, but is not limited to DNA (single-stranded, double-stranded, linear, covalently closed, super-coiled and relaxed circular forms) or RNA (single stranded, double stranded, linear or covalently closed), or a combination of DNA and RNA.

Nucleic Acid-Containing Mediums

As used herein, the term "medium" encompasses any biological material, either naturally occurring or scientifically engineered, which contains at least one nucleic acid in addition to other non-nucleic acid material, such as biomolecules (e.g., proteins, polysaccharides, lipids, low molecular weight enzyme inhibitors, oligonucleotides, primers, templates), polyacrylamide, trace metals, organic solvents, etc. Examples of naturally-occurring mediums include, but are not limited to, whole blood, blood plasma, and other body fluids, as well as tissue cell cultures obtained from humans, plants, or animals. Examples of scientifically-engineered mediums include, but are not limited to, lysates, nucleic acid samples eluted from agarose and/or polyacrylamide gels, solutions containing multiple species of nucleic acid molecules resulting either from nucleic acid amplification methods, such as polymerase chain reaction (PCR) amplification or reverse transcription polymerase chain reaction (RT-PCR) amplification, or from RNA or DNA size selection procedures, and solutions resulting from post-sequencing reactions.

Binding Matrix

Advantageously, one or more binding matrices can be used in the present invention. As used, herein, the term "binding matrix" encompasses any form capable of binding nucleic acid. Those skilled in the art will be able to select an appropriate binding matrix for use.

Examples of suitable binding matrices include MAGA-ZORB® paramagnetic particles (available from Promega, Madison, Wis., catalog item MB1001), GENFIND™ particles (available from BECKMAN-COULTER™, Fullerton, Calif.), MAGNESIL® Blue paramagnetic silica particles (available from Promega, catalog item A2201), zeolite particles (see Bitner et al., U.S. Published Patent Appln. No. 2007/0172855, the entirety of which is incorporated by reference herein), and paramagnetic apple or citrus pectin particles. Other suitable binding matrices include, without limitation, chemically modified cellulosic materials comprising vicinal diols, nylon, paramagnetic silica particles, cellulose membranes, and silica membranes. As a comparative example, silanated MAGNESIL® paramagnetic silica particles were also used (see Bitner et al., U.S. Pat. No. 6,787, 307, the entirety of which is incorporated by reference herein).

Formulation

The formulation acts as a lysis and/or binding solution that separates the nucleic acid of interest from its in vivo cellular environment and, if a binding matrix is present, facilitates the binding of the nucleic acid to the binding matrix. As mentioned above, the formulation may contain an amount of proteinase K, 1-thioglycerol, lysis solutions, CHAPS, TERGITOL™ type NP-9, TRITON™ X-100, GTC and an amount of acetamide and/or one or more acetamide derivatives.

If GTC-A is used, the respective amounts of GTC and acetamide and/or acetamide derivative(s) present in a GTC-A formulation can be adjusted to various concentrations. The concentration of GTC in the formulation is preferably from approximately 2.6M to approximately 4.3M. The concentration of acetamide and/or acetamide derivative(s) in the formulation is preferably from approximately 5.0M to approximately 7.0M.

GTC can be purchased from Promega, catalog item V2791. Acetamide can be purchased from SIGMA-ALDRICH™, catalog item A0500-500G. As mentioned, GTC can also be used with derivatives of acetamide. Preferred acetamide derivatives include N-methylacetamide (available from ACROS of Fair Lawn, N.J., catalog item 126141000) and N,N-dimethylacetamide (available from SIGMA-ALDRICH™, catalog item D5511). Sometimes, such as when purifying DNA, RNA or a combination of DNA and RNA from HEK293 tissue cells, the use of GTC and N,N-dimethylacetamide is preferred over the use of GTC and acetamide or GTC and N-methylacetamide.

Optionally, a GTC-A formulation can further contain one or more additional ingredients such as, for example, proteinase K, 1-TG, digitonin, lysis solutions, CHAPS, TERGITOL™ type NP-9, and TRITON™ X-100.

In addition to being used as a lysis and/or binding solution, the GTC-A formulation can also be used as a wash solution for removing impurities, as described in the methods below.

Kits

A kit comprises a binding matrix, a first formulation providing binding conditions wherein the amount of nucleic acid bound to the binding matrix is essentially independent of the amount of surface area of the definable amount of the binding matrix, and a second formulation providing binding conditions wherein the amount of nucleic acid bound to the definable amount of binding matrix is essentially dependent on the amount of surface area of the definable amount of the binding matrix.

In a preferred embodiment, the first formulation comprises polyethylene glycol of 8,000 molecular weight between 5% and 12% and NaCl from 0.5M to 1.5M, and a second formulation that comprises guanidine thiocyanate from 2.6M to 4.3M, and acetamide, or N-methylacetamide, or N,N dimethylacetamide or a combination thereof, from 5.0M to 7.0M.

In another preferred embodiment, for the purification of RNA or a combination of DNA and RNA, the first binding formulation may comprise 1,2 propane diol and a salt (e.g. NaCl, sodium citrate), or a combination of 1,2 propane diol, salt and an alcohol.

The formulation can be combined with one or more binding matrices in a kit that can be used in the purification of nucleic acids. Preferably, the ratio of binding matrix to formulation in the kit is within the range of from 1:400 to 1:1, by volume. The preferred amount of binding matrix is dependent on the preferred predetermined amount of nucleic acid that is desired using the second binding condition. The ratio of binding matrix to formulation can be varied within or outside of this preferred range, depending on the specific contents of the kit and the application for which the kit is intended.

Advantageously, the kit can include more than one type of binding matrix, each compatible with DNA, RNA, or both DNA and RNA. In this case, the kit can be used in the selective purification of different amounts of DNA, RNA, or DNA and RNA.

First Method

In one preferred implementation, the invention relates to a method of purifying a defined quantity of nucleic acid contained in a medium. The medium which contains nucleic acids is combined with a definable amount of a binding matrix and a formulation, the formulation being sufficient to cause the nucleic acid to separate from its in vivo cellular environment and bind to the binding matrix under a first set of binding conditions. The first set of binding conditions occurs when the amount of nucleic acid bound to the binding matrix is essentially independent of the amount of surface area of the definable amount of the binding matrix. The medium, binding matrix, and formulation can be combined in any order or simultaneously. The binding matrix with the nucleic acid bound thereto is then separated from substantially the rest of the combined medium and formulation, for example, by using a magnetic rack, by centrifuging, or by filtration.

Optionally, the binding matrix and the nucleic acid can be washed using a suitable wash solution, in order to remove any impurities. Thereafter, the at least one nucleic acid is eluted from the binding matrix, thereby obtaining the at least one nucleic acid in a substantially purified form. Furthermore, the nucleic acid can optionally be removed and stored. Accordingly, the elution step can immediately follow the aforementioned steps, or it can be performed at a later time. By choosing to elute the nucleic acid from the binding matrix at a later time, the nucleic acid can be stored for downstream activities.

Once the nucleic acid has been eluted, the nucleic acid is combined with the discrete quantity of binding matrix used in step (a), capable of reversibly binding nucleic acid, the amount of nucleic acid eluted being in excess of the binding capacity of the binding matrix under a second set of binding conditions. Under the second set of conditions, the amount of nucleic acid bound to the definable amount of binding matrix is essentially dependent on the amount of surface area of the definable amount of the binding matrix. The complex with the nucleic acid is removed from the medium and the nucleic acid is separated from the complex, whereby a defined quantity of nucleic acid is obtained. The separation can occur by, for example, eluting the nucleic acid.

In more detail, the elution steps use an elution buffer to separate the nucleic acid from the binding matrix, after which the substantially purified nucleic acid is contained in the elution buffer. Suitable elution buffers include, but are not limited to, nuclease-free water or aqueous solutions such as, for example, TRIS™-HCl, TRIS™-acetate, sucrose, and formamide solutions. A preferred elution buffer is a TRIS™ buffer with ethylenediaminetetraacetic acid (EDTA). More preferably, the elution buffer is about 10 mM Tris (pH 8.0) and about 1 mM EDTA. Elution of the nucleic acid from the binding matrix occurs quickly (e.g., in thirty seconds or less) when a suitable low ionic strength elution buffer is used.

Following purification, the nucleic acid can be used for any of a number of known scientific procedures, including, without limitation, the isolation of genetic material, polymerase chain reactions, electrophoresis, sequencing, cloning, and the like. One of the advantages of the foregoing method is that for certain types of biological samples, such as human whole blood, tissue samples or soil samples, wherein the composition of the biological sample varies within a relatively wide range (e.g. lipid composition and white blood cell number both vary widely between donors of human whole blood, and soil samples may vary widely in pH or salinity, which can increase the variability of the amount of nucleic acid binding to a binding matrix), the purification of nucleic acid under the first set of binding conditions reduces the variable composition of samples, which thereby reduces the range of variability in the amounts of nucleic acid obtained using the second set of binding conditions.

Another advantage, which is optional, is that the method allows for both the separate archiving of a portion of the nucleic acid purified under the first set of binding conditions, as well as, the purification of a defined amount of nucleic acid under the second set of binding conditions.

Second Method

In another embodiment, the present invention can be used in the purification of a defined quantity of DNA contained in a medium, such as whole blood, plasma, or tissue cell cultures obtained from humans, plants, or animals. The method includes steps of (a) combining the medium containing DNA with a definable amount of a binding matrix capable of reversibly binding DNA, and a formulation, the formulation being sufficient to cause the DNA to separate from its in vivo cellular environment and to bind to the binding matrix, under a first set of binding conditions, wherein the amount of DNA bound to the binding matrix is essentially independent of the amount of surface area of the definable amount of the binding matrix, (b) separating the binding matrix with DNA bound thereto from substantially the rest of the combined medium and formulation, (c) eluting the DNA from the binding matrix, thereby obtaining DNA in a substantially purified form, (d) using the discrete quantity of binding matrix used in step (a), the amount of DNA provided in step (c) being in excess of the binding capacity of the binding matrix under a second set of binding conditions, wherein the amount of DNA bound to the definable amount of binding matrix is essentially dependent on the amount of surface area of the definable amount of the binding matrix, (e) forming a complex of the binding matrix and the DNA by combining the binding matrix and the medium, under a second set of binding conditions wherein the amount of DNA bound to the definable amount of binding matrix is essentially dependent on the amount of surface area of the definable amount of the binding matrix, (f) removing the complex with the DNA from the medium, and (g) separating the DNA of step (f) from the complex, whereby a defined quantity of DNA is obtained.

This method is similar to the method mentioned above, however, it allows for the optimal purification of DNA.

Third Method

In yet another embodiment, the invention relates to the methods as described above, except that the separation and eluting steps are not required to be carried out, although such steps are not excluded. This method allows nucleic acid bound to the binding matrix to be stored for later use in other scientific procedures and downstream activities. Thus, the binding matrix with the nucleic acid bound thereto can form a complex of the binding matrix and the nucleic acid without separating from the binding matrix.

Example 1

In this example, DNA from human whole blood samples was purified. The following procedure was used:
1. Prepare 18 samples, 1-18, by adding 20 μl of proteinase K, followed by 200 μl of human whole blood (EDTA anticoagulated, available from Bioreclamation, Inc., Hicksville, N.Y., catalog item HMPLEDTA3), to 18 separate 1.5 ml plastic tubes.
2. Add 200 μl of Promega Lysis Buffer (available from Promega, catalog item MC501), to each of tubes 1-18. Mix each sample thoroughly.
3. Allow each sample to sit for about 20 minutes at about 56° C. then, allow each sample to sit for about 2 minutes at about 21° C.
4. Add 500 μl of Promega Binding Solution (available from Promega, catalog item MC502), to each of tubes 1-18. Mix each sample thoroughly.
5. Allow each sample to sit for about 2 minutes at about 21° C. then, add the following particles to each of samples 1-18 as follows: (a) to each of samples 1-4, add 20 μl of MAGAZORB® paramagnetic particles; (b) to each of samples 5-8, add 10 μl of MAGAZORB® paramagnetic particles; (c) to each of samples 9-12, add 5 μl of MAGAZORB® paramagnetic particles; (d) to each of samples 13-16 add 2.5 μl of MAGAZORB® paramagnetic particles; (e) to sample 17, add 20 μl of silanated MAGNESIL™ paramagnetic silica particles, and (f) to sample 18, add 10 μl of silanated MAGNESIL™ paramagnetic silica particles. The silanated MAGNESIL™ paramagnetic silica particles serve as negative controls. Vortex each sample every 2-3 minutes for about 20 minutes at a temperature of about 21° C.
6. Magnetize the samples by placing them on a magnetic rack for about 2 minutes. Remove the excess fluid, so that only the magnetized particles remain.
7. Remove the samples from the magnetic rack and wash each sample by adding 1 ml of Promega Wash Solution (available from Promega, catalog item MC504) and mixing by, for example, vortexing. Next, magnetize the samples by placing them back on the magnetic rack for an additional 2 minutes. Remove the excess fluid, so that only the magnetized particles remain.
8. Remove the samples from the magnetic rack and elute the DNA from the particles by adding 200 μl of nuclease free water to each sample for about 20 minutes at a temperature of about 56° C.
9. If clumping occurs in any of the samples, mix the sample by pipetting, first using a P1000 tip, and then a narrower bore P200 tip. This will break up the clump of particles and DNA.
10. Using blue/orange 6X loading dye (available from Promega, catalog item G190), load 5 μl of the samples per lane into a 1% agarose gel (available from Cambrex Bio Science, Rockland, Me., catalog item 54907). Lanes 1-4: 20 μl of particles; lanes 5-8: 10 μl of particles; lanes 9-12: 5 μl of particles; lanes 13-15: 2.5 μl of particles; lanes 16-17: Promega genomic DNA (G304); lane 18: Promega 100 bp ladder; lane 19: 20 μl silanated MAGNESIL™ particles; lane 20: 10 μl silanated MAGNESIL™.
11. Perform electrophoresis using bromphenol blue dye at 120 volts for about 3 hours or until the bromphenol blue dye reaches the bottom slit of the gel. Stain for 15 minutes with SYBR™ Gold (available from INVITROGEN™, catalog item S11494), and digitally image all of the lanes using an ALPHA INNOTECH FLUOROCHEM™ Imaging System, and, in particular, the Amersham TYPHOON™ platform with settings of: 1. ex488/em526. 2. PMT 450.

FIG. 1 shows the results of the electrophoresis analysis of the 18 samples prepared according to Example 1. In FIG. 1, the lanes are numbered 1-20, from left to right. As demonstrated in FIG. 1, in the case of human whole blood, the use of MAGAZORB® paramagnetic particles achieved substantial purification of genomic DNA. All concentrations of MAGAZORB® paramagnetic particles resulted in substantial DNA purification. Lane 16, which purified DNA using 2.5 µl of particles, shows at least as much DNA as that obtained using 20 µl of particles. This ability to purify large amounts of DNA, using either larger amounts of particles or smaller amounts of particles is sometimes referred to herein as the MaxYield method.

Example 2

In this example, DNA from human whole blood samples was purified using the MaxYield method together with a formulation and binding matrix, different from the binding matrix of Example 1. The following procedure was used:
1. Prepare 18 samples, 1-18, by adding 20 µl of proteinase K, followed by 200 µl of human whole blood, to each of eighteen 1.5 ml plastic tubes.
2. Add 200 µl of Promega Lysis Buffer to each of tubes 1-18. Mix each sample thoroughly by, for example, vortexing.
3. Allow each sample to sit for about 20 minutes at about 56° C. then, allow each sample to sit for about 2 minutes at about 21° C.
4. Add 500 µl of Promega Binding Solution, to each of tubes 1-18. Mix each sample thoroughly by, for example, vortexing.
5. Allow each sample to sit for about 2 minutes at 21° C., then add the following particles to each of samples 1-18 as follows: (a) to each of samples 1-4, add 20 µl of paramagnetic zeolite particles; (b) to each of samples 5-8, add 10 µl of paramagnetic zeolite particles; (c) to each of samples 9-12, add 5 µl of paramagnetic zeolite particles; (d) to each of samples 13-16 add 2.5 µl of paramagnetic zeolite particles; (e) to sample 17, add 20 µl of DNA-IQ™ paramagnetic particles, and (f) to sample 18, add 10 µl of DNA-IQ™ paramagnetic particles. The DNA-IQ™ paramagnetic particles (available from Promega, catalog item DC6701), serve as negative controls. Mix each sample by vortexing every 2-3 minutes for about 20 minutes at a temperature of about 21° C.
6. Magnetize the samples by placing them on a magnetic rack for 2 minutes. Remove the excess fluid, so that only the magnetized particles remain.
7. Remove the samples from the magnetic rack and wash each sample by adding 1 ml of Promega Wash Solution and mix by vortexing. Next, magnetize the samples by placing them back on the magnetic rack for an additional 2 minutes. Remove the excess fluid, so only the magnetized particles remain.
8. Remove the samples from the magnetic rack and elute the DNA from the particles by adding 200 µl of nuclease free water to each sample for about 20 minutes at a temperature of about 56° C.
9. If clumping occurs in any of the samples, mix the sample by pipetting, first using a P1000 tip, and then a narrower bore P200 tip. This will break up the clump of particles and DNA.
10. Using blue/orange 6X loading dye, load 5 µl of the DNA-containing, nuclease-free water from each of samples 1-18. Lanes 1-4: 20 µl of particles; lanes 5-8: 10 µl of particles; lanes 9-12: 5 µl of particles; lanes 13-16: 2.5 µl of particles; lane 17: Promega 100 bp DNA ladder; lane 18: Promega genomic DNA (G304); lane 19: 20 µl DNA-IQ™ resin; lane 20: 10 µl DNA-IQ™ resin.
11. Perform electrophoresis using bromphenol blue dye at 120 volts for about 3 hours or until the bromphenol blue dye reaches the bottom slit of the gel. Stain for 15 minutes with SYBR™ Gold, and digitally image all of the lanes using an ALPHA INNOTECH FLUOROCHEM™ Imaging System and, in particular, the Amersham TYPHOON™ platform with settings of: 1. ex488/em526. 2. PMT 450.

Figure 2:
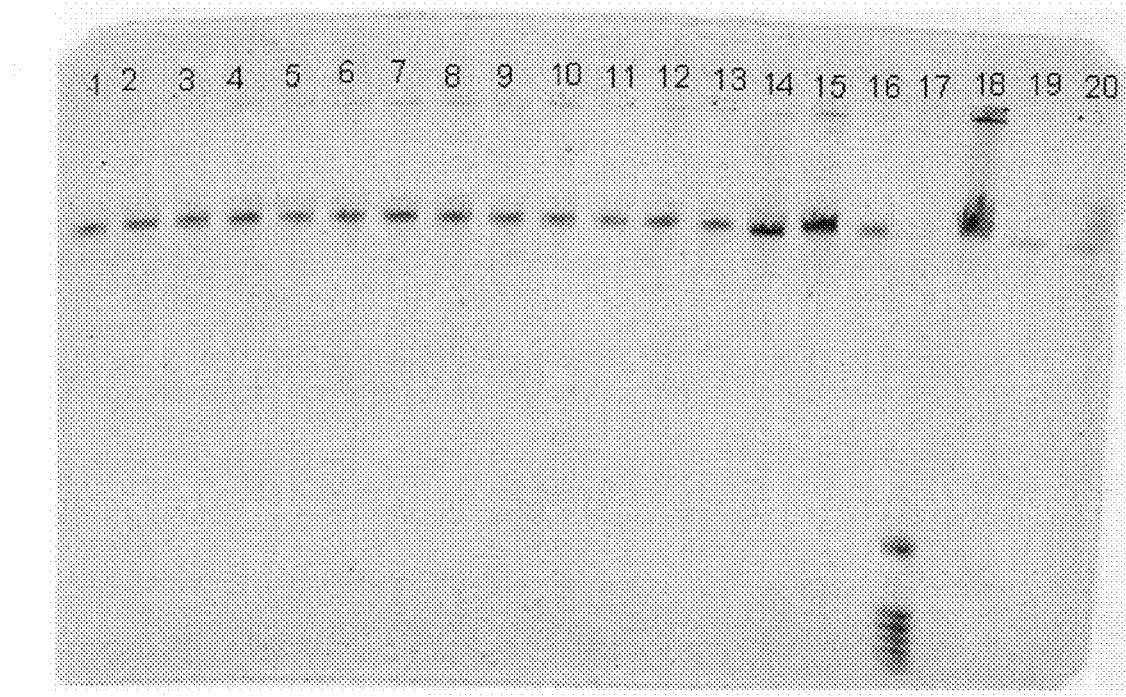
FIG. 2 is a photograph showing the results of an electrophoresis analysis performed in accordance with Example 2, described below.

FIG. 2 shows the results of the electrophoresis analysis of the 18 samples prepared according to Example 1. In FIG. 2, the lanes are numbered 1-20, from left to right. Lanes 1-16, 19, and 20 show the results for samples 1-16, 19, and 20, respectively; lane 18 shows genomic DNA standard; and lane 17 shows the 100 bp DNA ladder of standard molecular weight.

As shown in FIG. 2, in the case of human whole blood, all concentrations of paramagnetic zeolite particles resulted in substantial DNA purification, and the amounts of DNA purified were largely independent of the amount of particles used in the purification.

Example 3

In this example, DNA from 200 µl human whole blood was purified with a DNA-IQ™ method using a GTC-A formulation and binding matrix. The following procedure was used:
1. Prepare "$D_X$-A," which consists of 4.0M GTC, 5.0M acetamide, 20% (volume/volume) 1-TG, 0.64% (weight/volume) CHAPS, 0.64% (volume/volume) TERGITOL™ type NP-9, and 0.16% (volume/volume) TRITON™ X-100 in a 15ml plastic tube.
2. To the 4 ml of $D_X$-A, add 2 ml of human whole blood and thoroughly mix by, for example, vortexing. Add 2 ml of nuclease free water and mix by, for example, vortexing.
3. Prepare fifteen samples, 1-15 by adding 500 µl of the new combination to each of fifteen 1.5 ml plastic tubes, then add the following particles to each of samples 1-15 as follows: (a) to each of samples 1-3, add 20 µl of MAGAZORB® paramagnetic particles; (b) to each of samples 4-6, add 10 µl of MAGAZORB® paramagnetic particles; (c) to each of samples 7-9, add 5 µl of MAGAZORB® paramagnetic particles; (d) to each of samples 10-12 add 2.5 µl of MAGAZORB® paramagnetic particles; and (e) to samples 13-15, add 1.25 µl of MAGAZORB® paramagnetic particles. Mix each sample by vortexing for about 10 minutes at about 21° C.
4. Magnetize the samples by placing them on a magnetic rack for about 2 minutes. Remove the excess fluid, so that only the magnetized particles remain.
5. Remove the samples from the magnetic rack and wash each sample by adding 500 µl of $D_X$-A and then mix by, for example, vortexing. Next, magnetize the samples by placing them back on the magnetic rack for an additional 1 minute. Remove the excess fluid, so only the magnetized particles remain.
6. For each of samples 1-15, repeat the wash procedure of step 5, five more times using 500 µl of $D_X$-A each time.
7. Wash each sample twice with 500 µl of a mixture of 2.6M GTC and 7.1M acetamide, using the wash procedure of step 5, except substituting the GTC-A mixture for $D_X$-A.
8. Remove the samples from the magnetic rack and elute the DNA from the particles by adding 100 µl of nuclease free water to each sample.
9. Using blue/orange 6X loading dye, load 5 µl of the DNA-containing nuclease free water from each of samples 1-15 into a respective one of fifteen agarose gel electrophoresis lanes contained in two 15% TBE-urea gels.

14. Perform electrophoresis using bromphenol blue dye at 120 volts for about 3 hours or until the bromphenol blue dye reaches the bottom slit of the gel. Stain for 15 minutes with SYBR™ Gold, and digitally image all of the lanes using an ALPHA INNOTECH FLUOROCHEM™ Imaging System, and, in particular, the Amersham TYPHOON™ platform with settings of: 1. ex488/em526. 2. PMT 450.

Figure 3A:
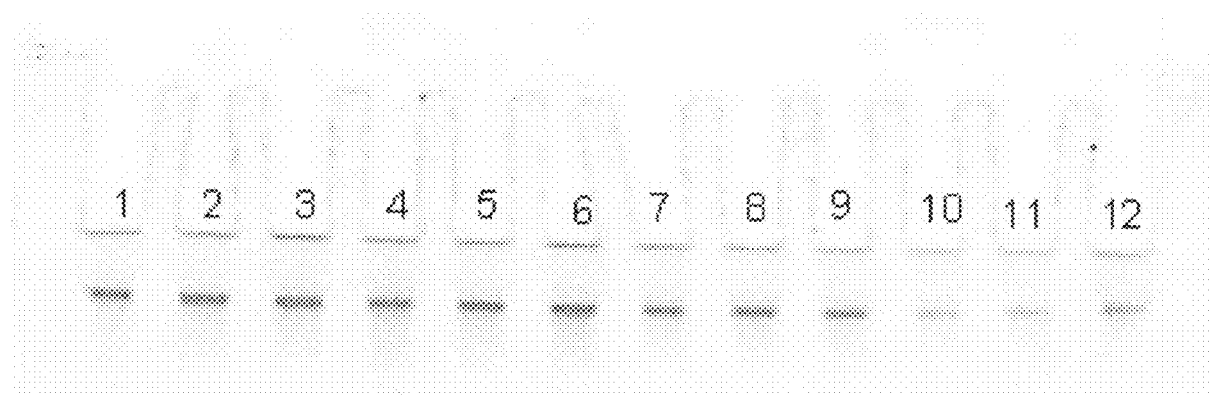
FIGS. 3A and 3B are photographs showing the results of an electrophoresis analysis performed in accordance with Example 3, described below.
Figure 3B:
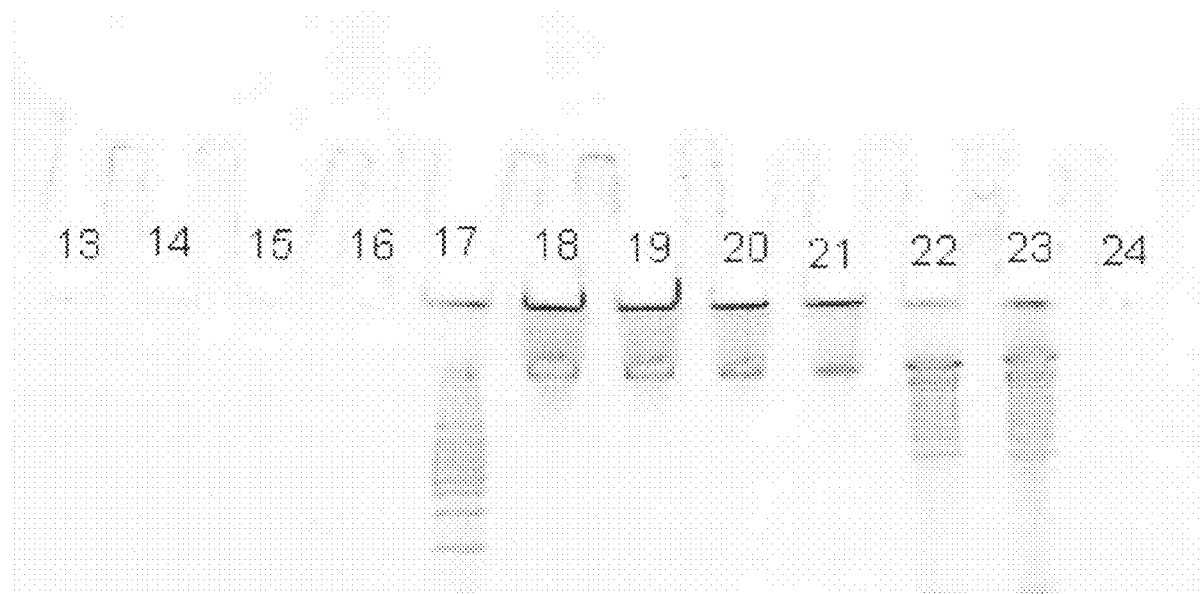

FIGS. 3A and 3B show the results of the electrophoresis analysis of the fifteen samples prepared according to Example 3. In FIG. 3A, the lanes are numbered 1-12, from left to right. In FIG. 3B, the lanes are numbered 13-24, from left to right. Lanes 1-15 show the results for samples 1-15, respectively; lane 16 is empty; lane 17 shows the 100 bp DNA ladder of standard molecular weight; lane 18 shows Promega 326 ng genomic DNA; lane 19 shows Promega 163 ng genomic DNA; lane 20 shows Promega 82 ng genomic DNA; lane 21 shows Promega 41 ng genomic DNA; lanes 22 and 23 show Promega DNA markers. Lane 24 is empty.

As shown in FIGS. 3A and 3B, in the case of human whole blood, all of the samples prepared in accordance with Example 3 achieved DNA purification using this "DNA-IQ™" method using a GTC-A formulation and MAGAZORB® paramagnetic particles. In contrast to the MaxYield method shown in Examples 1 and 2, using this DNA-IQ™ method, as the amount of particles used per sample decreased, the amount of DNA purified similarly decreased. Table 1 shows the results of the DNA yields of the samples from Example 3 as performed through PICOGREEN® assay, which was performed according to the manufacturer's directions.

TABLE 1

| MAGAZORB® paramagnetic particles (μl) | Concentration of DNA (ng/μl) | Average Concentration |
|---|---|---|
| 20 μl A | 1.82 | 1.531483 |
| 20 μl B | 0.88 | |
| 20 μl C | 1.90 | |
| 10 μl A | 1.05 | 0.823651 |
| 10 μl B | 0.88 | |
| 10 μl C | 0.54 | |
| 5 μl A | 1.19 | 0.550287 |
| 5 μl B | 0.19 | |
| 5 μl C | 0.27 | |
| 2.5 μl A | 0.14 | 0.129339 |
| 2.5 μl B | 0.15 | |
| 2.5 μl C | 0.10 | |
| 1.25 μl A | 0.09 | 0.046405 |
| 1.25 μl B | 0.03 | |
| 1.25 μl C | 0.03 | |

Example 4

In this example, DNA from human whole blood samples was released using the DNA-IQ™ method with a GTC-A formulation and a binding matrix, different from the binding matrix of Example 3. The following procedure was used:

1. Prepare "$D_X$-A" which consists of 4.0M GTC, 5.0M acetamide, 20% (volume/volume) 1-TG, 0.64% (weight/volume) CHAPS, 0.64% (volume/volume) TERGITOL™ type NP-9, and 0.16% (volume/volume) TRITON™ X-100 in a 15 ml plastic tube.

2. To 4 ml of $D_X$-A, add 2 ml of human whole blood and mix the combination by, for example, vortexing. Add 2 ml of nuclease free water and mix the new combination by, for example, vortexing.

3. Prepare fifteen samples, 1-15 by adding 500 μl of the new combination to each of fifteen 1.5 ml plastic tubes, then add the following particles to each of samples 1-15 as follows: (a) to each of samples 1-3, add 20 μl of paramagnetic zeolite particles; (b) to each of samples 4-6, add 10 μl of paramagnetic zeolite particles; (c) to each of samples 7-9, add 5 μl of paramagnetic zeolite particles; (d) to each of samples 10-12 add 2.5 μl of paramagnetic zeolite particles; and (e) to samples 13-15, add 1.25 μl of paramagnetic zeolite particles. Mix each sample by vortexing and incubate for about 10 minutes at about 21° C.

4. Magnetize the samples by placing them on a magnetic rack for about 2 minutes. Remove the excess fluid, so that only the magnetized particles remain.

5. Remove the samples from the magnetic rack and wash each sample by adding 500 μl of $D_X$-A and mix by, for example, vortexing. Next, magnetize the samples by placing them back on the magnetic rack for an additional 1 minute. Remove the excess fluid, so that only the magnetized particles remain.

6. For each of samples 1-15, repeat the wash procedure of step 5 seven more times using 500 μl of $D_X$-A each time.

7. Wash each sample twice with 500 μl of a mixture of 2.6M GTC and 7.1M acetamide, using the wash procedure of step 5.

8. Remove the samples from the magnetic rack and elute the DNA from the particles by adding 100 μl of nuclease free water to each sample.

9. Remove the elutions from the samples and place them in separate tubes numbered 1a-15a, corresponding to tubes 1-15, respectively. Then perform a second elution by adding 100 μl of nuclease free water to each of samples 1-15.

10. Again, remove the elutions from samples 1-15 and place the elutions in separate tubes numbered 1b-15b, corresponding to tubes 1-15, respectively. Then, perform a third elution by adding 100 μl of nuclease free water to each sample.

11. Add the respective a and b elution tubes to the third elution of its respective sample, i.e. add tubes 1a and 1b to sample 1. Combining the three elutions facilitates a more complete elution of samples from their respective particles.

12. Using blue/orange 6X loading dye, load 5 μl of the combined elution sample of the DNA-containing nuclease free water from each of samples 1-15 into a respective one of fifteen agarose gel electrophoresis lanes contained in a 15% TBE-urea gel.

13. Perform electrophoresis using bromphenol blue dye at 120 volts for about 3 hours or until the bromphenol blue dye reaches the bottom slit of the gel. Stain for 15 minutes with SYBR™ Gold, and digitally image all of the lanes using an ALPHA INNOTECH FLUOROCHEM™ Imaging System, and, in particular, the Amersham TYPHOON™ platform with settings of: 1. ex488/em526. 2. PMT 450.

Figure 4A:
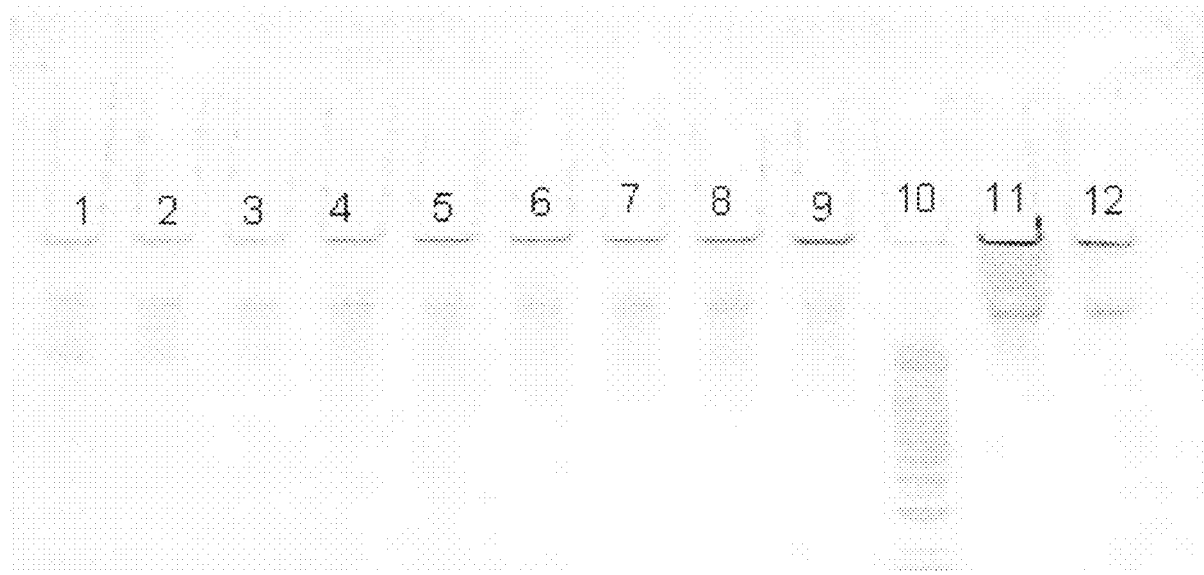
FIGS. 4A and 4B are photographs showing the results of an electrophoresis analysis performed in accordance with Example 4, described below.
Figure 4B:

FIGS. 4A and 4B show the results of the electrophoresis analysis of the fifteen samples prepared according to Example 4. In FIG. 4A, the lanes are numbered 1-12, from left to right. In FIG. 4B, the lanes are numbered 13-24, from left to right. Lanes 1-9 show the results for samples 1-9, respectively; lane 10 shows the 100 bp DNA ladder of standard molecular weight; lane 11 shows Promega 320 ng genomic DNA; lane 12 shows Promega 81 ng genomic DNA; lanes 13-18 shows the results for samples 10-15, respectively; lane 19 is empty; lane 20 shows 100 bp DNA ladder of standard molecular weight; lane 21 shows Promega 160 ng genomic DNA; lane 22 shows Promega 80 ng genomic DNA; lane 23 shows Promega 40 ng genomic DNA. Lane 24 is empty.

As shown in FIGS. 4A and 4B, in the case of human whole blood, all of the samples prepared in accordance with Example 4 achieved DNA purification using the DNA-IQ™ method in combination with a GTC-A formulation and paramagnetic zeolite particles. In agreement with the results of Example 3, and in contrast to the MaxYield method shown in Examples 1 and 2, using this DNA-IQ™ method shows that as the amount of particles used per sample decreases, the amount of DNA purified correspondingly decreases.

Example 5

In this example, DNA from human whole blood samples was released with a MaxYield method using a formulation containing polyethylene glycol 8000 and NaCl and a binding matrix, followed by a DNA-IQ™ method using a GTC-A formulation and the binding matrix. The following procedure was used:

1. Prepare twelve samples, 1-12, by adding 20 µl of proteinase K, followed by 200 µl of human whole blood, to each of twelve 1.5 ml plastic tubes. To tubes numbered 1, 2, 5, 6, 9, and 10, add blood from donor L, and add to tubes 3, 4, 7, 8, 11, and 12, blood from donor H.
2. Add 200 µl of Promega Lysis Buffer to each sample. Mix each sample thoroughly by vortexing.
3. Incubate each sample for about 10 minutes at about 56° C.
4. Add 500 µl of Promega Binding Solution, to each sample. Mix each sample thoroughly by, for example, vortexing.
5. Allow each sample to sit for about 2 minutes at about 21° C., then add the following particles to each of samples 1-12 as follows: (a) to each of samples 1-4, add 10 µl of MAGAZORB® paramagnetic particles; (b) to each of samples 5-8, add 5 µl of MAGAZORB® paramagnetic particles; and (c) to each of samples 9-12, add 2.5 µl of MAGAZORB® paramagnetic particles. Mix each sample by vortexing every 2-3 minutes for about 10 minutes at about 21° C.
6. Magnetize the samples by placing them on a magnetic rack for about 2 minutes. Remove the excess fluid, so that only the magnetized particles remain.
7. Remove the samples from the magnetic rack and wash each sample by adding 1 ml of Promega Wash Solution and then mix by vortexing. Next, magnetize the samples by placing them back on the magnetic rack for an additional 5 minutes. Remove excess fluid, so that only the magnetized particles remain.
8. Remove the samples from the magnetic rack and elute the DNA from the particles by adding 200 µl of nuclease free water to each sample for about 10 minutes at about 21° C.
9. Magnetize the samples by placing them on a magnetic rack for about 1 minute. Remove 10 µl of elution from each of samples 1-12, placing them in clean 1.5 ml plastic tubes numbered 13-24, respectively. (Although only 10 µl of elution is set aside, it is possible to set aside greater amounts of the samples for later analysis while leaving the samples with purified DNA in excess of the amount which can be bound by the binding matrix in the following steps).
10. Prepare "$L_X$" which consists of 4.0M GTC, 5.0M acetamide, and 20% (volume/volume) 1-TG.
11. Remove the samples from the magnetic rack and wash each sample by adding 300 µl of $L_X$ and mixing by vortexing. Incubate the samples for about 5 minutes at about 21° C. Next, magnetize the samples by placing them back on the magnetic rack for an additional 1 minute. Remove the excess fluid, so that only the magnetized particles remain for each sample.
12. For each sample, repeat the wash procedure of step 11 using 500 µl of $L_X$.
13. Wash each sample with 500 µl of a mixture of 2.6M GTC and 7.1M acetamide, using the wash procedure of step 11, substituting the $L_X$ with the GTC-A formulation.
14. Then, wash each sample with 500 µl of Promega Wash Solution, using the wash procedure of step 11, substituting the $L_X$ for Promega Wash Solution.
15. Remove the samples from the magnetic rack and elute the DNA from the particles by adding 100 µl of nuclease free water to each sample.
16. After magnetic separation of samples 1-12, using blue/orange 6X loading dye, load 5 µl from each of samples 1-12 and 10 µl of elution samples 13-24 into a respective one of twenty-four agarose gel electrophoresis lanes containing a 15% TBE-urea gel.
17. Perform electrophoresis using bromphenol blue dye at 120 volts for about 3 hours or until the bromphenol blue dye reaches the bottom slit of the gel. Stain for 15 minutes with SYBR™ Gold, and digitally image all of the lanes using an ALPHA INNOTECH FLUOROCHEM™ Imaging System, and, in particular, the Amersham TYPHOON™ platform with settings of: 1. ex488/em526. 2. PMT 450.

Figure 5A:
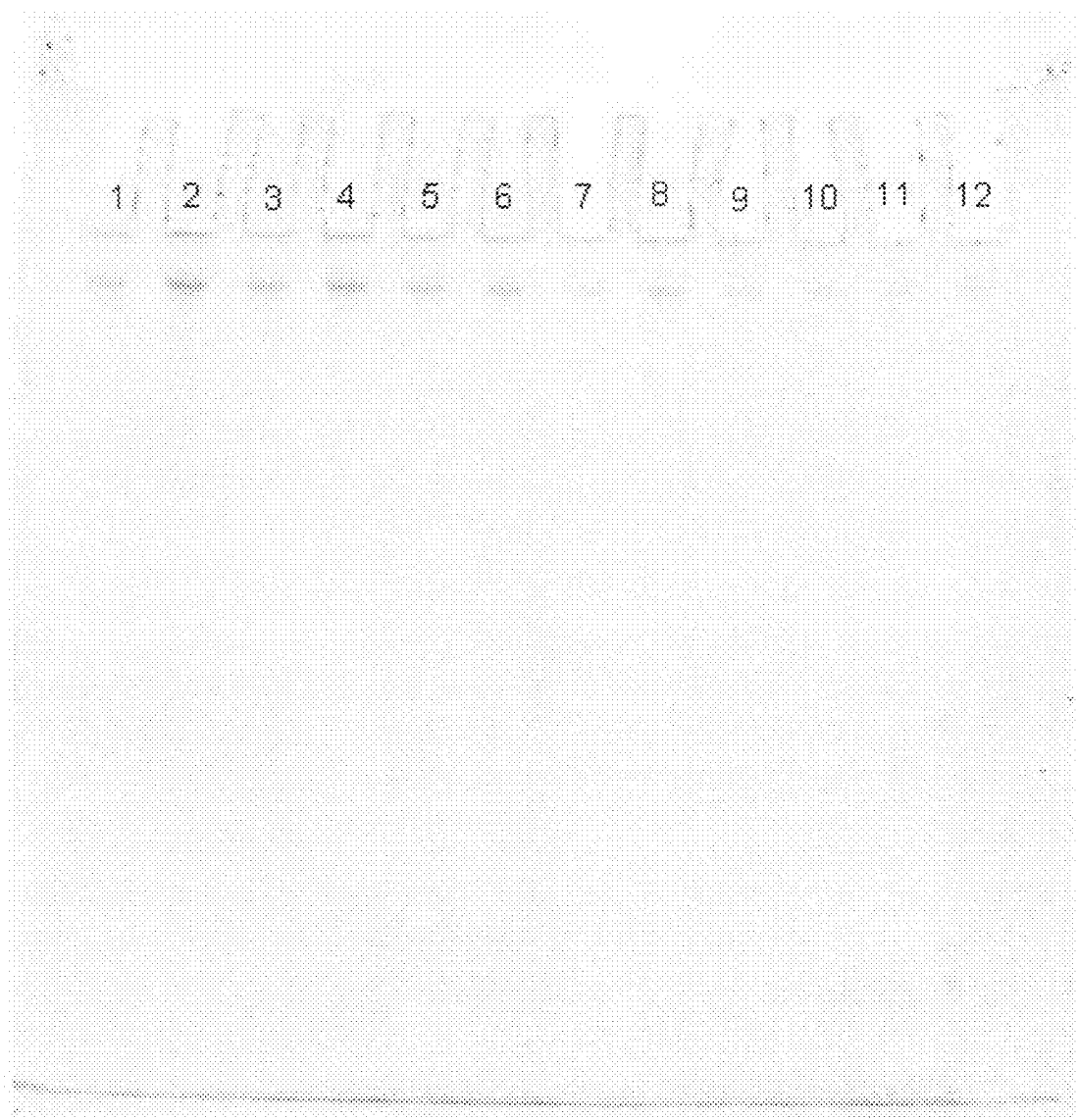
FIGS. 5A and 5B are photographs showing the results of an electrophoresis analysis performed in accordance with Example 5, described below.
Figure 5B:
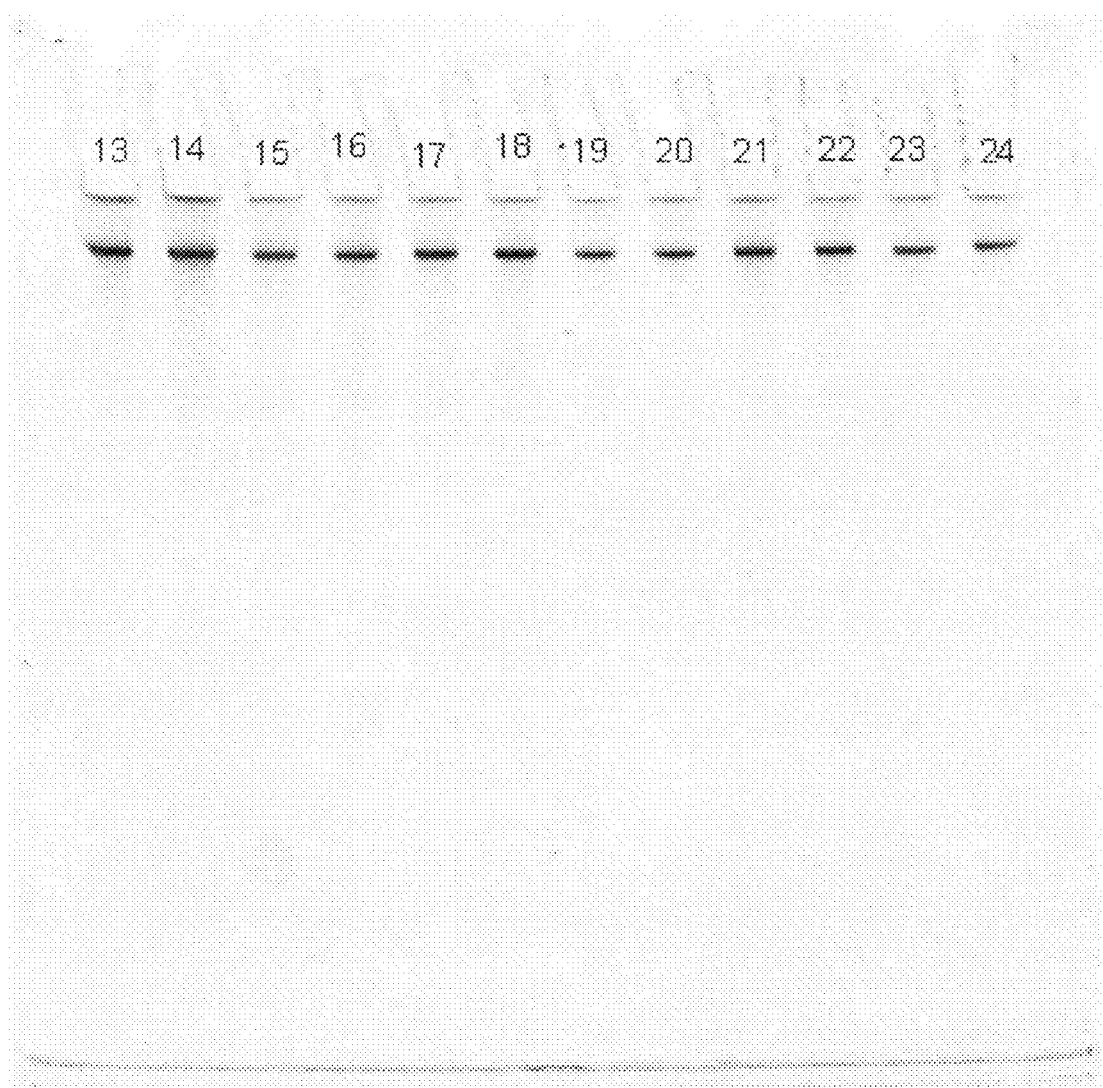

FIGS. 5A and 5B show the results of the electrophoresis analysis of the twenty-four samples prepared according to Example 5. In FIG. 5A, the lanes are numbered 1-12, from left to right. In FIG. 5B, the lanes are numbered 13-24, from left to right. Lanes 1 and 2: 10 µl of MAGAZORB™ particles with blood donor L, lanes 3 and 4: 10 µl of MAGAZORB™ particles with blood donor H, lanes 5 and 6: 5 µl of MAGAZORB™ particles with blood donor L, lanes 7 and 8: 5 µl of MAGAZORB™ with blood donor H, lanes 9 and 10: 2.5 µl of MAGAZORB™ particles with blood donor L, lanes 11 and 12: 2.5 µl of MAGAZORB™ particles with blood donor H, lanes 13-24 show 10 µl of 200 µl of the PEG/NaCl elutions which were removed in step 9, lanes 13 and 14: 10 µl of MAGAZORB™ particles with blood donor L, lanes 15 and 16: 10 µl of MAGAZORB™ particles with blood donor H, lanes 17 and 18: 5 µl of MAGAZORB™ particles with blood donor L, lanes 19 and 20: 5 µl of MAGAZORB™ particles with blood donor H, Lanes 21 and 22: 2.5 µl of MAGAZORB™ 8: 5 µl of MAGAZORB™ particles with blood donor L, lanes 23 and 24: 2.5 µl of MAGAZORB™ particles with blood donor H.

As shown in FIGS. 5A AND 5B, in the case of human whole blood, the use of a GTC-A formulation in combination with a binding matrix in the DNA-IQ™ method samples allowed the purification of genomic DNA from each of the samples prepared according to Example 5. Increased amounts of particles used per sample correspond to increased amounts of DNA in the final purification.

In this example, DNA from three different human whole blood donors was purified using two separate purification methods. The DNA yields using the MaxYield-DNA-IQ™ method (MaxYield followed by DNA-IQ™) were compared to the DNA yields obtained using the DNA-IQ™ method. The following procedure was used:

A. Purification of DNA using the DNA-IQ™ method with blood from three donors.

1. To each well of columns 1-6 of a deep well 96 plate (available from Promega, item V6771) add 5 µl of MAGAZORB® paramagnetic particles, using a single tip pipetter, for a total of 48 wells. Each column represents one sample, which is replicated 8 times, in each of the eight wells per column
2. Add 400 µl of one of the following formulations to a different one of samples 1-6 as follows: (a) to samples (columns) 1-3 and 5, add $D_X$; (b) to samples (columns) 4 and 6, add "$D_{X-MMA}$," which consists of 4.0M GTC, 5.0M N,N-dimethylacetamide, 20% (volume/volume) 1-TG, 0.64% (weight/volume) CHAPS, 0.64% (volume/volume) TERGITOL™ type NP-9, and 0.16% (volume/volume) TRITON™ X-100. Mix each sample thoroughly by repeated pipetting with an eight tip multichannel manual pipetter.
3. Add 150 µl of human whole blood from one of the following donors to a different one of samples 1-6 as follows: (a) to samples 1 and 2, add blood from donor A; (b) to samples 3 and 4, add blood from donor B; and (c) to samples 5 and 6, add blood from donor C. Mix each sample by pipetting with an eight tip multi-channel manual pipetter for about 2 minutes, and then incubate each sample for about 10 minutes at about 21° C. Add 200 µl of nuclease free water to each of the 64 wells, and mix thoroughly with an 8 tip multichannel manual pipetter.
4. Magnetize the samples by placing them on a magnetic rack for about 2 minutes, specifically, a Deep Well MAGNABOT® 96 Magnetic Separation Device (available from Promega, catalog item V3031). Remove the excess fluid, so that only the magnetized particles remain for each sample.
5. Remove the samples from the magnetic rack and wash samples 1-6 with 400 µl per well (for each of 8 wells per sample) of the following wash solutions: (a) wash samples 1-3 and 5 with $D_X$-A; and (b) wash samples 4 and 6 with freshly made $D_{X-MMA}$. Mix each sample thoroughly by repeated pipetting with an eight tip multi-channel manual pipetter for about 2 minutes. Next, magnetize the samples by placing them back on the magnetic rack for an additional 1 minute. Remove the excess fluid, so that only the magnetized particles remain for each sample.
6. For each sample, repeat the wash procedure of step 5 an additional six times using the same wash solutions for each sample.
7. Wash each sample with 400 µl of Promega Wash Solution, using the wash procedure of step 5, except substituting the respective wash solutions for Promega Wash Solution.
8. Remove the samples from the magnetic rack and elute the DNA from the particles by adding 100 µl of nuclease free water to each sample for about 20 minutes at about 21° C., then store the samples at about −20° C.
9. After magnetic separation of samples 1-6, using blue/orange 6× loading dye, load 10 µl of the eluted sample from each of the 8 wells per sample into their respective one of forty-eight agarose gel electrophoresis lanes contained in 15% TBE-urea gels.
10. Perform electrophoresis using bromphenol blue dye at 120 volts for about 3 hours or until the bromphenol blue dye reaches the bottom slit of the gel. Stain for 15 minutes with SYBR™ Gold, and digitally image all of the lanes using an ALPHA INNOTECH FLUOROCHEM™ Imaging System, and, in particular, the Amersham TYPHOON™ platform with settings of: 1. ex488/em526. 2. PMT 450.

B. Purification of DNA using the MaxYield-DNA-IQ™ method with blood from a three donors.

1. Prepare forty-eight samples, 1-48, by adding 15 µl of proteinase K to each of forty-eight wells in columns 1-6 of a round bottom deep 96 well plate. As above, each sample (columns 1-6) contains 8 replicate wells.
2. Add 150 µl of human whole blood from one of the following donors to each well of samples 1-6 as follows: (a) to each of samples 1 and 2 (columns 1 and 2, 16 wells total), add 150 µl blood per well from donor A; (b) to each of samples 3 and 4 (columns 3 and 4, 16 wells total), add 150 µl blood per well from donor B; and (c) to each of samples 4 and 5 (columns 4 and 5, 16 wells total), add 150 µl blood per well from donor C. 150 µl of Promega Lysis Solution (available from Promega, catalog item MC501) was added per well, for all 48 wells. Mix each sample by pipetting with an eight tip multi-channel manual pipetter for about 2 minutes, and then incubate each sample for about 10 minutes at about 21° C.
3. Add 375 µl of Promega Binding Buffer (available from Promega, catalog item MC502) to each sample.
4. Add 5 µl of MAGAZORB® paramagnetic particles, to each of the 48 wells, using a single tip pipetter. Mix each sample by pipetting with an eight tip multi-channel manual pipetter for about 2 minutes, and then incubate each sample for about 10 minutes at about 21° C.
5. Magnetize the samples by placing them on a magnetic rack for about 2 minutes, specifically, a Deep Well MAGNABOT® 96 Magnetic Separation Device. Remove the excess fluid, so that only the magnetized particles remain.
6. Remove the samples from the magnetic rack and wash the samples with 500 µl of Promega Wash Solution (MC504). Next, magnetize the samples by placing them back on the magnetic rack for an additional 2 minutes. Remove the excess fluid, so that only the magnetized particles remain for each sample.
7. Remove the samples from the magnetic rack. Elute the DNA from the particles by adding 100 µl of nuclease free water to each sample for about 15 minutes at about 21° C. (using an 8 channel multi-channel pipetter to mix).
8. Magnetize the samples by placing them back on the magnetic rack for about 1 minute. Remove 20 µl of each sample well and store in a clean round bottom deep 96 well plates at about −20° C. for future use (including some samples used for lanes 1-3 of FIG. 6). Remove the samples from the magnetic rack and then resuspend the particles in each sample using an eight tip multi-channel manual pipetter.
9. Add 400 µl of one of the following formulations to a different one of sample wells 1-48 as follows: (a) to each of sample wells 1-24, and 33-40, add $D_X$; (b) to each of samples 25-32, and 41-48, add "$D_{X-MMA}$," which consists of 4.0M GTC, 5.0M N,N-dimethylacetamide, 10% (volume/volume) 1-TG, 0.64% (weight/volume) CHAPS, 0.64% (volume/volume) TERGITOL™ type NP-9, and 0.16% (volume/volume) TRITON™ X-100.

Mix each sample thoroughly by repeated pipetting with an eight tip multi-channel manual pipetter for about 2 minutes, and then incubate each sample for about 10 minutes at about 21° C.

10. Magnetize the samples by placing them on a magnetic rack for about 1 minute. Remove the excess fluid, so that only the magnetized particles remain.
11. Remove the samples from the magnetic rack and wash each sample with 500 µl of $D_{X}$-A or freshly made $D_{X\text{-}MMA}$, whichever was used in the binding formulation. Mix each sample thoroughly by repeated pipetting with an eight tip multi-channel manual pipetter for about 2 minutes. Next, magnetize the samples by placing them back on the magnetic rack for an additional 1 minute. Remove the excess fluid, so that only the magnetized particles remain.
12. Wash each sample with 500 µl of Promega Wash Solution, using the wash procedure of step 5, except substituting $D_{X}$-A or $D_{X\text{-}MMA}$, whichever was used per sample, with Promega Wash Solution.
13. Remove the samples from the magnetic rack and elute the DNA from the particles by adding 100 µl of nuclease free water to each sample for about 20 minutes at about 21° C., then store the samples at about −20° C.
14. After magnetic separation of samples 1-48, using blue/orange 6× loading dye, load 10 µl of each eluted sample into a respective one of forty-eight agarose gel electrophoresis lanes containing a 15% TBE-urea gel.
15. Perform electrophoresis using bromphenol blue dye at 120 volts for about 3 hours or until the bromphenol blue dye reaches the bottom slit of the gel. Stain for 15 minutes with SYBR™ Gold, and digitally image all of the lanes using an ALPHA INNOTECH FLUORO-CHEM™ Imaging System, and, in particular, the Amersham TYPHOON™ platform with settings of: 1. ex488/em526. 2. PMT 450.

Figure 6:
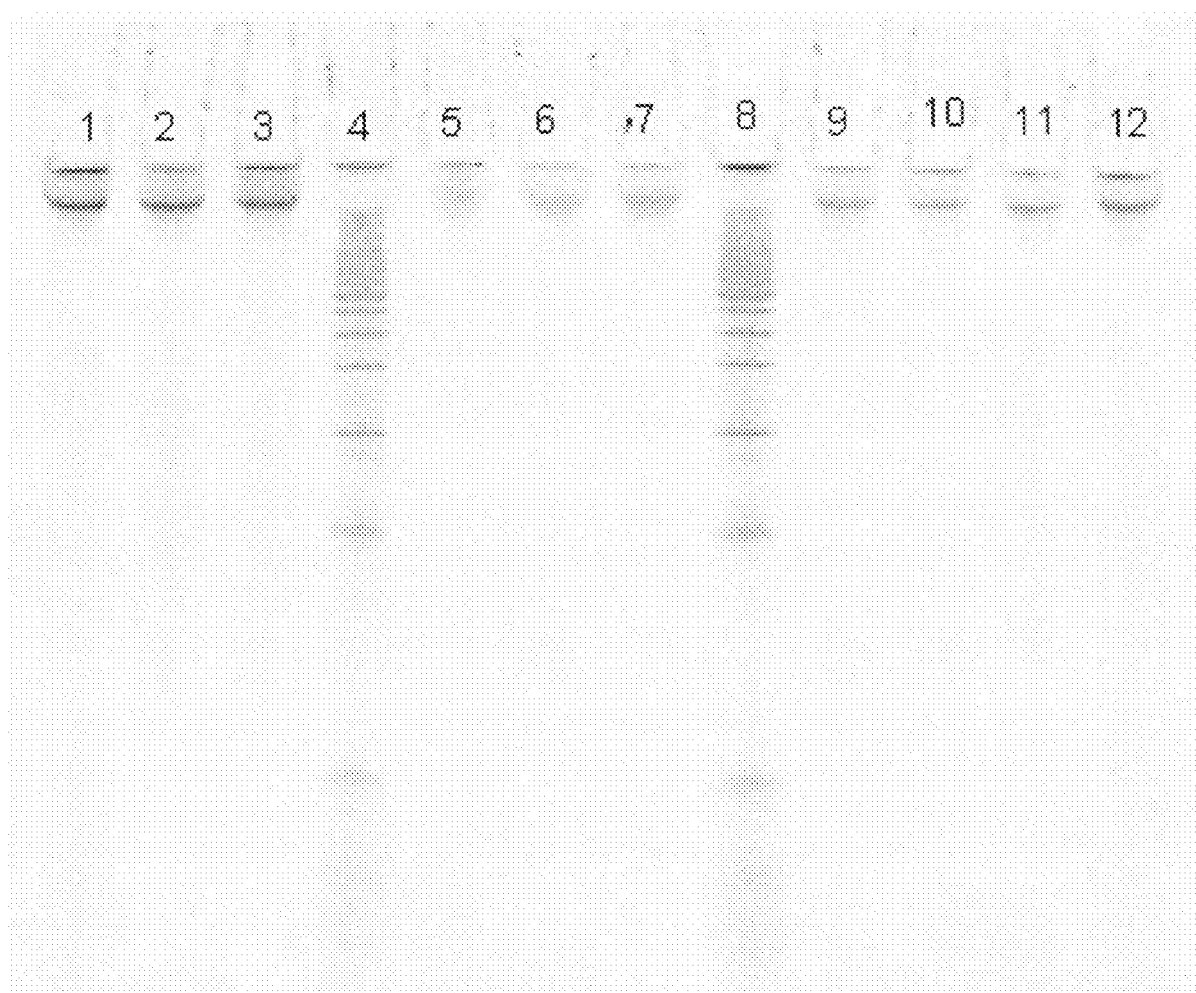
FIG. 6 is a photograph showing the results of an electrophoresis analysis performed in accordance with Example 6, described below.

FIG. 6 shows the results of the electrophoresis analysis of some of the samples prepared according to Examples 6A and 6B. In FIG. 6, the lanes are numbered 1-12, from left to right. Lanes 1-3 show the results for DNA purified using the archived MaxYield samples from step 8 of the method of Example 6B for blood donors A-C, respectively; lane 4 and lane 8: Promega 100 bp DNA Ladder; lanes 5-7 show the DNA from the same donors, respectively, purified with the DNA-IQ™ method using GTC-A ($D_{X}$-A) formulation of Example 6A for blood donors A-C, respectively; lanes 9-12 show the results for DNA purified using the MaxYield-DNA-IQ™ method and using the GTC-MMA ($D_{X\text{-}MMA}$) formulation with N,N-dimethyl acetamide of Example 6B for blood donors A-C, respectively.

As shown in FIG. 6, in the case of human whole blood, for all three donors, the MaxYield DNA from 6B step 8 provided DNA in excess of the binding capacity of the 5 µl of particles, under the conditions used for the subsequent DNA-IQ™ steps as described in Example 6B.

Table 2 shows the results of the DNA yields of the samples from Examples 6A and 6B as performed using PICOGREEN®. The DNA yields of the MaxYield-DNA-IQ™ and DNA-IQ™ methods are represented in the table below. Table 2 shows that the use of the DNA-IQ™ method directly on blood provides greater variability in DNA concentration (ng/ul) (0.45 to 6.1) between blood donors than does the MaxYield-DNA-IQ™ method which shows arithmetic averages from 1.36 to 1.94 ng/ul (if the 1D sample (4.91) were excluded, the average of the first 7 samples would be 1.52, and the arithmetic averages of all three blood donors would range from 1.36 to 1.71 using the MaxYield-DNA-IQ™ method).

TABLE 2

| Donor & Sample # | MaxYield-DNA-IQ™ (ng/µl) | Average Concentration | Standard Deviation | DNA-IQ™ (ng/µl) | Average Concentration | Standard Deviation |
|---|---|---|---|---|---|---|
| Donor A/Sample 1 | 2.34 | | | 1.08 | | |
| Donor A/Sample 2 | 1.16 | | | 1.08 | | |
| Donor A/Sample 3 | 1.24 | | | 0.73 | | |
| Donor A/Sample 4 | 4.91 | | | 1.63 | | |
| Donor A/Sample 5 | 1.22 | | | 1.14 | | |
| Donor A/Sample 6 | 1.3 | | | 0.94 | | |
| Donor A/Sample 7 | 1.87 | 1.522857 | 0.245467068 | 1.12 | | |
| Donor A/Sample 8 | 1.53 | 1.94625 | 0.294333198 | 1.36 | 1.135 | 0.159099026 |
| Donor A/Sample 9 | 1.9 | | | 1.35 | | |
| Donor A/Sample 10 | 1.86 | | | 0.98 | | |
| Donor A/Sample 11 | 1.52 | | | 0.48 | | |
| Donor A/Sample 12 | 1.18 | | | 0.75 | | |
| Donor A/Sample 13 | 1.52 | | | 1 | | |
| Donor A/Sample 14 | 1.77 | | | 1.16 | | |
| Donor A/Sample 15 | 1.63 | | | 0.8 | | |
| Donor A/Sample 16 | 1.77 | 1.64375 | 0.089272231 | 1.21 | 0.96625 | 0.172357278 |
| Donor B/Sample 17 | 1.73 | | | 0.79 | | |
| Donor B/Sample 18 | 0.97 | | | 0.85 | | |
| Donor B/Sample 19 | 1.05 | | | 0.13 | | |
| Donor B/Sample 20 | 1.11 | | | 0.5 | | |
| Donor B/Sample 21 | 2.63 | | | 0.87 | | |
| Donor B/Sample 22 | 1.08 | | | 0.69 | | |
| Donor B/Sample 23 | 0.98 | | | 0.76 | | |
| Donor B/Sample 24 | 1.39 | 1.3675 | 0.015909903 | 1.06 | 0.70625 | 0.250139024 |
| Donor B/Sample 25 | 1.44 | | | 0.55 | | |
| Donor B/Sample 26 | 1.08 | | | 0.42 | | |
| Donor B/Sample 27 | 1.6 | | | 0.14 | | |
| Donor B/Sample 28 | 1.36 | | | 0.27 | | |
| Donor B/Sample 29 | 2.03 | | | 0.63 | | |
| Donor B/Sample 30 | 0.84 | | | 0.61 | | |
| Donor B/Sample 31 | 1.15 | | | 0.24 | | |

TABLE 2-continued

| Donor & Sample # | MaxYield-DNA-IQ™ (ng/μl) | Average Concentration | Standard Deviation | DNA-IQ™ (ng/μl) | Average Concentration | Standard Deviation |
|---|---|---|---|---|---|---|
| Donor B/Sample 32 | 2.41 | 1.48875 | 0.651422122 | 0.72 | 0.4475 | 0.192686598 |
| Donor C/Sample 33 | 1.36 | | | 0.82 | | |
| Donor C/Sample 34 | 2.03 | | | 0.79 | | |
| Donor C/Sample 35 | 0.84 | | | 0.95 | | |
| Donor C/Sample 36 | 1.15 | | | 0.47 | | |
| Donor C/Sample 37 | 2.41 | | | 0.87 | | |
| Donor C/Sample 38 | 1.36 | | | 0.96 | | |
| Donor C/Sample 39 | 0.99 | | | 0.51 | | |
| Donor C/Sample 40 | 2.21 | 1.54375 | 0.471109893 | 0.95 | 0.79 | 0.113137085 |
| Donor C/Sample 41 | 1.19 | | | 6.88 | | |
| Donor C/Sample 42 | 1.33 | | | 5.26 | | |
| Donor C/Sample 43 | 1.79 | | | 7.3 | | |
| Donor C/Sample 44 | 1.46 | | | 5.87 | | |
| Donor C/Sample 45 | 1.52 | | | 5.83 | | |
| Donor C/Sample 46 | 2.32 | | | 7.43 | | |
| Donor C/Sample 47 | 1.77 | | | 5.68 | | |
| Donor C/Sample 48 | 2.3 | 1.71 | 0.417193001 | 4.47 | 6.09 | 1.145512986 |

Example 7

In this example, DNA from two different human whole blood donors was purified using two different DNA binding matrices. The yields of the MaxYield-DNA-IQ™ method were compared to the yields of the DNA-IQ™ method. The following procedure was used:

A. Purification of DNA using the DNA-IQ™ method with blood from two donors.
1. Prepare four samples, 1-4, each with 8 replicates, in columns 1-4, respectively, of a deep well 96 plate (available from Promega, item V6771), by adding 5 μl of one of the following binding matrices per well to one of samples 1-4 as follows: (a) to each of samples 1 and 2 (columns 1 and 2, 8 wells per column), add MAGAZORB® paramagnetic particles; and (b) to each of samples 3 and 4, add paramagnetic zeolite particles. Each sample contains 8 wells per column.
2. To each sample, add 400 μl per well of freshly made "$D_{X-MA}$," which consists of 4.0M GTC, 5.0M N-methylacetamide, 10% (volume/volume) 1-TG, 0.64% (weight/volume) CHAPS, 0.64% (volume/volume) TERGITOL™ type NP-9, and 0.16% (volume/volume) TRITON™ X-100. Mix each sample thoroughly by repeated pipetting with an eight tip multi-channel manual pipetter for about 2 minutes.
3. Add 150 μl of human whole blood from one of the following donors to a different one of samples 1-4 as follows: (a) to each well of samples 1 and 3, add blood from donor A; and (b) to each well of samples 2 and 4, add blood from donor B. Mix each sample by pipetting with an eight tip multi-channel manual pipetter for about 2 minutes, and then incubate samples for about 10 minutes at about 21° C.
4. Magnetize the samples by placing them on a magnetic rack for about 2 minutes, specifically, a Deep Well MAGNABOT® 96 Magnetic Separation Device. Remove the excess fluid, so that only the magnetized particles remain.
5. Remove the samples from the magnetic rack and wash samples 1-4 with 400 μl per well of a wash solution consisting of 4.0M GTC and 5.0M methylacetamide. Mix each sample thoroughly by repeated pipetting with an eight tip multi-channel manual pipetter for about 2 minutes. Next, magnetize the samples by placing them back on the magnetic rack for an additional 1 minute. Remove the excess fluid, so that only the magnetized particles remain for each sample.
6. For each sample, repeat the wash procedure of step 5 an additional six times using the same wash solutions for each sample.
7. Wash each sample with 400 μl per well of Promega Wash Solution, using the wash procedure of step 5, except substituting the respective wash solutions for Promega Wash Solution.
8. Remove the samples from the magnetic rack and elute the DNA from the particles by adding 100 μl of nuclease free water to each sample well for about 20 minutes at about 21° C., then store the samples at about −20° C.

B. Purification of DNA with the MaxYield-DNA-IQ™ method using two blood donors.
1. Prepare four samples, in 4 columns of a deep well 96 well plate, 8 replicate sample wells per column, by adding 15 μl of proteinase K to each well.
2. Add 150 μl of human whole blood from one of the following donors to a different one of samples 1-4 as follows: (a) to each of the 8 wells of samples 1 and 3, add blood from donor A; and (b) to each of the 8 wells of samples 2 and 4, add blood from donor B. 150 μl of Promega Lysis Solution (available from Promega, catalog item MC501) was added per well, for all 32 wells. Mix each sample by pipetting with an eight tip multi-channel manual pipetter for about 2 minutes, and then incubate each sample for about 10 minutes at about 21° C.
3. Add 375 μl of Promega Binding Buffer to each sample well.
4. Add 5 μl of one of the following binding matrices to each well of samples 1-4 (columns 1-4) as follows: (a) to each of the 8 wells of samples 1 and 2, add MAGAZORB® paramagnetic particles; and (b) to each of the 8 wells of samples 3 and 4, add paramagnetic zeolite particles. Mix each sample by pipetting with an eight tip multi-channel manual pipetter for about 2 minutes, and then incubate each sample for about 10 minutes at about 21° C.
5. Magnetize the samples by placing them on a magnetic rack for about 2 minutes, specifically, a Deep Well MAGNABOT® 96 Magnetic Separation Device. Remove the excess fluid, so that only the magnetized particles remain.

6. Remove the samples from the magnetic rack and wash the samples with 500 µl of Promega Wash Solution per well. Next, magnetize the samples by placing them back on the magnetic rack for an additional 2 minutes. Remove the excess fluid, so that only the magnetized particles remain for each sample.
7. Remove the samples from the magnetic rack and elute the DNA from the particles by adding 100 µl of nuclease free water to each sample well for about 15 minutes at a temperature of about 21° C.
8. Magnetize the samples by placing them back on the magnetic rack for about 1 minute. Remove 20 µl from each sample well and store on a clean round bottom deep 96 well plate at about −20° C. for future use. Remove the samples from the magnetic rack and then resuspend the particles in each sample using an eight tip multi-channel manual pipetter.
9. Add freshly made 400 µl $D_{X-MA}$ to each of the 8 wells of samples 1 and 2 (columns 1 and 2). Mix each sample thoroughly by repeated pipetting with an eight tip multi-channel manual pipetter for about 2 minutes, and then incubate each sample for about 10 minutes at about 21° C.
10. Magnetize the samples by placing them on a magnetic rack for about 1 minute. Remove the excess fluid, so that only the magnetized particles remain.
11. Remove the samples from the magnetic rack and wash each sample well with 500 µl of a mixture of 4.0M GTC and 5.0M acetamide. Mix each sample thoroughly by repeated pipetting with an eight tip multi-channel manual pipetter for about 2 minutes. Next, magnetize the samples by placing them back on the magnetic rack for an additional 1 minute. Remove the excess fluid, so that only the magnetized particles remain for each sample.
12. Wash each sample well with 500 µl of Promega Wash Solution, using the wash procedure of step 11, except substituting the GTC-A formulation with Promega Wash Solution.
13. Remove the samples from the magnetic rack and elute the DNA from the particles by adding 100 µl of nuclease free water to each sample well for about 20 minutes at about 21° C., then store the samples at about −20° C.
14. After magnetic separation of samples 1-4, using blue/orange 6× loading dye, load 10 µl per well of each eluted sample of the DNA-containing nuclease free water from each of the samples into a respective one of forty-eight agarose gel electrophoresis lanes containing a 15% TBE-urea gel.
15. Perform electrophoresis using bromphenol blue dye at 120 volts for about 3 hours or until the bromphenol blue dye reaches the bottom slit of the gel. Stain for 15 minutes with SYBR™ Gold, and digitally image all of the lanes using an ALPHA INNOTECH FLUOROCHEM™ Imaging System, and, in particular, the Amersham TYPHOON™ platform with settings of: 1. ex488/em526. 2. PMT 450.

Table 3 shows the results of the DNA yields of samples from Examples 7A and 7B as performed using PICOGREEN®. The yields of the MaxYield-DNA-IQ™ and DNA-IQ™ methods are represented in the tables below. Both the MaxYield-DNA-IQ™ and DNA-IQ™ methods provide discrete quantities of purified DNA with narrow ranges of concentrations. Generally, the MaxYield-DNA-IQ™ method showed less variability between samples taken from different blood donors, as compared to the DNA-IQ™ method.

TABLE 3

| Donor & Sample # | MaxYield-DNA-IQ™ (ng/µl) | Average Concentration | Standard Deviation | DNA-IQ™ (ng/µl) | Average Concentration | Standard Deviation |
|---|---|---|---|---|---|---|
| Donor A/Sample 1 | 0.53 | | | 0.05 | | |
| Donor A/Sample 2 | 0.50 | | | 0.09 | | |
| Donor A/Sample 3 | 0.56 | | | 0.09 | | |
| Donor A/Sample 4 | 0.58 | | | 0.06 | | |
| Donor A/Sample 5 | 0.51 | | | 0.1 | | |
| Donor A/Sample 6 | 0.48 | | | 0.31 | | |
| Donor A/Sample 7 | 0.38 | | | 0.29 | | |
| Donor A/Sample 8 | 0.35 | 0.486 | 0.083 | 0.36 | 0.169 | 0.128 |
| Donor B/Sample 9 | 0.57 | | | 0.07 | | |
| Donor B/Sample 10 | 0.43 | | | 0.08 | | |
| Donor B/Sample 11 | 0.52 | | | 0.05 | | |
| Donor B/Sample 12 | 0.49 | | | 0.04 | | |
| Donor B/Sample 13 | 0.41 | | | 0.05 | | |
| Donor B/Sample 14 | 0.46 | | | 0.04 | | |
| Donor B/Sample 15 | 0.41 | | | 0.04 | | |
| Donor B/Sample 16 | 0.55 | 0.479 | 0.062 | 0.05 | 0.053 | 0.015 |
| Donor A/Sample 17 | 0.04 | | | 0.03 | | |
| Donor A/Sample 18 | 0.16 | | | 0.02 | | |
| Donor A/Sample 19 | 0.05 | | | 0.03 | | |
| Donor A/Sample 20 | 0.92 | | | 0.02 | | |
| Donor A/Sample 21 | 0.09 | | | 0.05 | | |
| Donor A/Sample 22 | 0.22 | | | 0.02 | | |
| Donor A/Sample 23 | 0.17 | | | 0.02 | | |
| Donor A/Sample 24 | 0.27 | 0.241 | 0.286 | 0.03 | 0.028 | 0.010 |
| Donor B/Sample 25 | 0.22 | | | 0.03 | | |
| Donor B/Sample 26 | 0.15 | | | 0.03 | | |
| Donor B/Sample 27 | 0.07 | | | 0.07 | | |
| Donor B/Sample 28 | 0.23 | | | 0.03 | | |
| Donor B/Sample 29 | 0.22 | | | 0.05 | | |
| Donor B/Sample 30 | 0.13 | | | 0.05 | | |
| Donor B/Sample 31 | 0.09 | | | 0.04 | | |
| Donor B/Sample 32 | 0.05 | 0.145 | 0.073 | 0.04 | 0.043 | 0.014 |

Although this invention has been described in certain specific exemplary embodiments, many additional modifications and variations would be apparent to those skilled in the art in light of this disclosure. It is, therefore, to be understood that this invention may be practiced otherwise than as specifically described. Thus, the exemplary embodiments of the invention should be considered in all respects to be illustrative and not restrictive, and the scope of the invention to be determined by any claims supported by this application, and the equivalents thereof, rather than by the foregoing description.

I claim:

1. A method of purifying a defined quantity of nucleic acid, the nucleic acid being present in an in vivo cellular environment, the nucleic acid and in vivo cellular environment being contained in a medium, the method comprising:
(a) combining the medium containing nucleic acid with a definable amount of a binding matrix capable of reversibly binding nucleic acid, and a first formulation, the first formulation being sufficient to cause the nucleic acid to separate from its in vivo cellular environment and to bind to the binding matrix, under a first set of binding conditions, wherein the amount of nucleic acid bound to the binding matrix is essentially independent of the amount of surface area of the definable amount of the binding matrix;
(b) separating the binding matrix with nucleic acid bound thereto from substantially the rest of the combined medium and formulation;
(c) eluting the nucleic acid from the binding matrix, thereby obtaining nucleic acid in a substantially purified form;
(d) forming a complex of the binding matrix used in step (a) after the elution of the matrix in step (c) and the nucleic acid eluted in step (c) by combining the binding matrix, a second formulation, and the nucleic acid and the medium, under a second set of binding conditions, wherein the amount of nucleic acid bound to the definable amount of binding matrix is essentially dependent on the amount of surface area of the definable amount of the binding matrix;
(e) removing the complex formed in step (d) with the nucleic acid bound thereto from the medium, and
(f) separating the nucleic acid of step (e) from the complex, whereby a defined quantity of nucleic acid is obtained.

2. The method of claim 1, wherein the binding matrix comprises one or more materials selected from the group consisting of paramagnetic cellulose particles, paramagnetic zeolite particles, paramagnetic silica particles, silica membranes, chemically modified cellulosic materials comprising vicinal diols, zeolite, and nylon.

3. The method of claim 1, wherein the nucleic acid obtained is genomic DNA, plasmid DNA, viral DNA, DNA obtained from a DNA amplification reaction, RNA, viral RNA, RNA obtained from a RNA amplification reaction, or a combination of one or more of the above.

4. The method of claim 1, wherein the first formulation comprises one or more materials selected from the group consisting of proteinase K, 1-thioglycerol, lysis solutions, polyethylene glycol, NaCl, 1,2 propane diol, 3-[(3-cholamidopropyl)dimethylammonio]-1-propanesulfonate, 26-(4-nonylphenoxy)-3,6,9,12,15,18,21,24-octaoxahexaconsan-1-ol, and 4-(1,1,3,3-tetramethylbutyl)phenyl-polyethylene glycol.

5. The method of claim 1, wherein the second formulation comprises one or more materials selected from the group consisting of proteinase K, 1-thioglycerol, lysis solutions, 3-[(3-cholamidopropyl)dimethylammonio]-1-propanesulfonate, 26-(4-nonylphenoxy)-3,6,9,12,15,18,21,24-octaoxahexaconsan-1-ol, 4-(1,1,3,3-tetramethylbutyl)phenyl-polyethylene glycol, guanidine thiocyanate, acetamide, methylacetamide and dimethylacetamide.

6. The method of claim 5, wherein the second formulation comprises guanidine thiocyanate, present in a concentration from approximately 2.6M to approximately 4.3M, and the concentration of the acetamide, the one or more acetamide derivatives, or the combination of acetamide and one or more acetamide derivatives in the second formulation is from approximately 5.0M to approximately 7.0M.

7. The method of claim 1, wherein a portion of the nucleic acid eluted in step (c) is removed prior to continuing with step (d).

8. The method of claim 4, wherein the first formulation comprises polyethylene glycol present in an amount of approximately 5% (weight to volume) to 12% (weight to volume), and NaCl present in a concentration from approximately 0.5M to 1.5M.

* * * * *